(12) United States Patent
White et al.

(10) Patent No.: US 10,481,126 B2
(45) Date of Patent: Nov. 19, 2019

(54) ELECTROLYTE-GATED TRANSISTORS FOR DETECTION OF MOLECULES

(71) Applicant: Regents of the University of Minnesota, Minneapolis, MN (US)

(72) Inventors: Scott P. White, Minneapolis, MN (US); C. Daniel Frisbie, Mahtomedi, MN (US); Kevin D. Dorfman, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 315 days.

(21) Appl. No.: 15/503,277

(22) PCT Filed: Aug. 13, 2015

(86) PCT No.: PCT/US2015/045108
§ 371 (c)(1),
(2) Date: Feb. 10, 2017

(87) PCT Pub. No.: WO2016/025743
PCT Pub. Date: Feb. 18, 2016

(65) Prior Publication Data
US 2017/0234830 A1  Aug. 17, 2017

Related U.S. Application Data

(60) Provisional application No. 62/037,352, filed on Aug. 14, 2014, provisional application No. 62/202,477, filed on Aug. 7, 2015.

(51) Int. Cl.
*G01N 27/414* (2006.01)
*C12Q 1/6869* (2018.01)
(Continued)

(52) U.S. Cl.
CPC ....... *G01N 27/4145* (2013.01); *C12Q 1/6869* (2013.01); *G01N 27/4161* (2013.01);
(Continued)

(58) Field of Classification Search
CPC .................. G01N 27/414; G01N 27/4145
See application file for complete search history.

(56) References Cited

U.S. PATENT DOCUMENTS 4,437,969 A * 3/1984 Covington ........... G01N 27/414
                                                              204/403.01
7,646,013 B2 * 1/2010 Herlogsson ......... H01L 51/0516
                                                              257/40
(Continued)

FOREIGN PATENT DOCUMENTS

| EP | 1669748 | 6/2006 |
| WO | WO2005015156 | 2/2005 |
| WO | WO2016025743 | 2/2016 |

OTHER PUBLICATIONS

Response to Examination Report dated Apr. 23, 2018, from counterpart European Application No. 15753592.3, filed Oct. 19, 2018, 12 pp.

(Continued)

*Primary Examiner* — Alexander S Noguerola
(74) *Attorney, Agent, or Firm* — Shumaker & Sieffert, P.A.

(57) ABSTRACT

The disclosure describes methods, devices, and system that measure chemisorption potentiometrically for detection of target molecules. In one example, a device includes a semiconductor, an ionic conducting electronic insulator coupled to the semiconductor, a floating gate electrode comprising a first portion and a second portion, the first portion being coupled to the semiconductor via the ionic conducting electronic insulator, an aqueous buffer, and a primary gate electrode coupled to the second portion of the (Continued)

floating gate electrode via the aqueous buffer. The second portion of the floating gate electrode may comprise a probe configured to react with a target chemical composition of a molecule to detect the presence of the molecule. Reaction with the target chemical composition may change an electrical property of the device and indicate the presence of the molecule in the aqueous buffer.

33 Claims, 27 Drawing Sheets

(51) Int. Cl.
GO1N 27/416 (2006.01)
GO1N 33/487 (2006.01)
H01L 51/05 (2006.01)
(52) U.S. Cl.
CPC ..... G01N 33/48721 (2013.01); H01L 51/052 (2013.01); H01L 51/0554 (2013.01)

(56) References Cited

U.S. PATENT DOCUMENTS

2010/0301398 A1 12/2010 Rothberg et al.
2014/0319466 A1* 10/2014 Dasgupta ............ H01L 51/0562 257/24

OTHER PUBLICATIONS

International Search Report and Written Opinion of International Application No. PCT/US2015/045108, dated Nov. 12, 2015, 13 pp.
International Preliminary Report on Patentability from International Application No. PCT/US2015/045108, dated Feb. 23, 2017, 8 pp.
Schmoltner et al., "Electrolyte-Gate Organic Field-Effect Transistor for Selective Reversible Ion Detection," Advanced Materials, first published Sep. 19, 2013, 5 pp.
White et al., "Label-Free DNA Sensing Platform with Low-Voltage Electrolyte-Gated Transistors," Analytical Chemistry, American Chemical Society, web publication Jan. 8, 2015, 6 pp.
Zhang et al., "Viscoelastic Properties, Ionic Conductivity, and Materials Design Considerations for Poly(styrene-b-ethylene oxide-b-styrene)- Based Ion Gel Electrolytes," Macromolecules, ACS Publications, web publication Oct. 28, 2011, 9 pp.
Kim et al., "Performance and Stability of Aerosol-Jet-Printed Electrolyte-Gated Transistors Based on Poly93-hexylthiophene)," Applied Materials & Interfaces, ACS Publications, web publication Jun. 18, 2013, 6 pp.
Peterson et al., "The Effect of Surface Probe Density on DNA Hybridization," Nucleic Acids Research, vol. 29, No. 24, Oxford University Press, Oct. 11, 2001, 6 pp.
Lai et al., "Ultralow Voltage, OTFT-Based Sensor for Label-Free DNA Detection," Advanced Materials, Oct. 2, 2012.
Kim et al., "Molecular Tunnel Junctions Based on π-Conjugated Oligoacene Thiols and Dithiols between Ag, Au, and Pt Contacts: Effect of Surface Linking Group and Metal Work Function," Journal of the American Chemical Society, ACS Publications, Oct. 21, 2011, 14 pp.
Hirons et al., "TOTO and YOYO: New Very Bright Fluorochromes for DNA Content Analyses by Flow Cytometry," Cytometry vol. 15, Issue 2, Wiley Online Library, Aug. 5, 1993, 12 pp.
Grimme et al., "Development of Fieldable Lab-on-a-Chip Systems for Detection of a Broad Array of Targets From Toxicants to Biowarefare Agents," Journal of Nanotechnology in Engineering and Medicine, vol. 4, May 2013, 8 pp.
Chan et al., "Evidence-Based Point-of-Care Diagnostics: Current Status and Emerging Technologies," Annual Review of Analytical Chemistry, vol. 6, Jun. 2013 but first published online Mar. 20, 2013, 23 pp.
Lin et al., "Organic Thin-Film Transistors for Chemical and Biological Sensing," Advanced Materials, Nov. 21, 2011, 18 pp.
Berggren et al., "Organic Bioelectronics," Advanced Materials, Sep. 25, 2007, 13 pp.
Zheng et al., "Label-free colorimetric assay for DNA methylation based on unmodified Au nanorods as a signal sensing probe coupled with enzyme-linkage reactions," Chemical Communication, Royal Science of Chemistry Publishing, Mar. 11, 2013, 3 pp.
Kim et al., Electrolyte-Gated Transistors for Organic and Printed Electronics, Advanced Materials, Dec. 2, 2012, 25 pp.
Buth et al., "Electrolyte-gated organic field-effect transistors for sensing applications," Applied Physics Letters, American Institute of Physics, Mar. 2011, 3 pp.
Lee et al., "Electrical Impedance of Spin-Coatable Ion Gel Films," The Journal of Physical Chemistry, ACS Publications, Mar. 16, 2011, 7 pp.
Lin et al., "Organic Electrochemical Transistors Integrated in Flexible Microfluidic Systems and Used for Label-Free DNA Sensing," Advanced Materials, Jul. 27, 2011, 6 pp.
Tang et al., "Carbon Nanotube DNA Sensor and Sensing Mechanism," Nano Letters, vol. 6, No. 8, Nano Letters, Aug. 2006, 7 pp.
Kergoat et al., "A Water-Gate Organic Field-Effect Transistor," Advanced Materials, May 20, 2010, 5 pp.
Kim et al., "An FET-type charge sensor for highly sensitive detection of DNA sequence," Biosensors and Bioelectronics, Elsevier, Mar. 19, 2004, 6 pp.
Gaikwad et al., A flexible high potential printed battery for powering printed electronics, Applied Physics Letters, AIP Publishing LLC, Jun. 12, 2013, 5 pp.
Herne et al., "Characterization of DNA Probes Immobilized on Gold Surfaces," Journal of American Chemical Society, vol. 119, Jun. 13, 1997, 7 pp.
Steel et al., "Immobilization of Nucleic Acids at Solid Surfaces: Effect of Oligonucleotide Length on Layer Assembly," Biophysical Journal, vol. 79, Aug. 2000, 7 pp.
Wong et al., "An Electrostatic Model for DNA Surface Hybridization," Biophysical Journal, vol. 98, Jun. 2010, 10 pp.
Minot et al., "Carbon nanotube biosensors: The critical role of the reference electrode," Applied Physics Letters, vol. 91, Aug. 28, 2007, 3 pp.
Chou et al., "Electrodeless Dielectrophoresis of Single- and Double-Stranded DNA," Biophysical Journal vol. 83, Oct. 2002, 10 pp.
Thompson et al., "Label-free detection of nucleic acid and protein microarrays by scanning Kelvin nanoprobe," Biosensors and Bioelectronics, vol. 20, Aug. 2004, 12 pp.
Chen et al., "Folded Floating-Gate CMOS Biosensor for the Detection of Charged Biochemical Molecules," IEEE Sensors Journal, vol. 11, No. 11, Nov. 2011, 5 pp.
Sinensky et al., "Label-free and high-resolution protein/DNA nanoarray analysis using Kelvin probe force microscopy," Nanotechnology, Nature Publishing Group, vol. 2, Sep. 23, 2007, 7 pp.
Hansen et al., Discerning Biomolecular Interactions Using Kelvin Probe Technology, American Chemical Society, May 29, 2003, published online Jul. 17, 2003, 7 pp.
Steel et al., "Electrochemical Quantitation of DNA Immobilized on Gold," Analytical Chemistry, vol. 70, No. 22, Nov. 15, 1998, American Chemical Society, published online Oct. 8, 1998, 8 pp.
Drummond et al., "Electrochemical DNA sensors," Nature Biotechnology, vol. 21, No. 10, Oct. 2003, 10 pp.
Holzel et al., "Dielectric and dielectrophoretic properties of DNA," IET Journals, vol. 3, Issue 2, The institution of Engineering and Technology, Dec. 8, 2008, 18 pp.
Guo et al., "Conductivity of a sing DNA duplex bridging a carbon nanotube gap," Nanotechnology, vol. 3, Feb. 10, 2008, 5 pp.
Peterson et al., "Hybridization of Mismatched or Partially Matched DNA at Surfaces," Journal of the American Chemical Society, vol. 124, No. 49, Dec. 11, 2002, 9 pp.
Friend et al., "Fabrication of microfluidic devices using polydimethylsiloxane," Biomicrofluidics, vol. 4, Issue 2, Jun. 2010, 5 pp.
Sackmann et al., "The present and future role of microfluidics in biomedical research," Nature, Practical Microfluidics, vol. 507, Issue 7491, Mar. 13, 2014, 11 pp.

(56) References Cited

OTHER PUBLICATIONS

Squires et al., "Making it stick: convection, reaction and diffusion in surface-based biosensors," Nature Biotechnology, Apr. 7, 2008, 10 pp.

Sassolas et al., "DNA Biosensors and Microarrays," Chemical Review, vol. 108, American Chemical Society, Jun. 21, 2007, published on web Dec. 21, 2007, 31 pp.

White et al., "Operating and Sensing Mechanism of Floating-Gate Transistors Utilizing Electrolyte Dielectrics," The Journal of Physical Chemistry, Dec. 10, 2015, 10 pp.

Tao et al., "A Novel Floating-Gate Biosensing Device with Controlled Charge-Modulation," Life Science Systems and Applications Workshop, Nov. 8-9, 2007, available online IEEE Dec. 10, 2007, 4 pp.

Bernards, et al., "Enzymatic sensing with organic electrochemical transistors," Journal of Materials Chemistry, vol. 18, The Royal Society of Chemistry, published online Oct. 12, 2007, 5 pp.

White et al., "Rapid, Selective, Label-Free Aptameric Capture and Detection of Ricin in Potable Liquids Using a Printed Floating Gate Transistor," Sensors ACS Publications, Sep. 20, 2016, 4 pp.

Kergoat et al., "Advances in organic transistor-based biosensors: from organic electrochemical transistors to electrolyte-gated organic field-effect transistors," Analytical and Bioanalytical Chemistry, vol. 402, Issue 5, Feb. 2012, Springer online, Sep. 11, 2001, 14 pp.

Gong et al., "DNA surface hybridization regimes," Proceedings of the National Academy of Sciences of the United States of America, vol. 105, No. 14, Apr. 8, 2008, 6 pp.

Khodagholy et al., "Organic electrochemical transistor incorporating an iongel as a solid state electrolyte for lactate sensing," Journals of Materials Chemistry, vol. 22, The Royal Society of Chemistry, Jan. 13, 2012, 4 pp.

Khodagholy et al., High transconductance organic electrochemical transistors, Nature Communications, Macmillan Publishers Limited, Jul. 12, 2013, 6 pp.

Lu et al., "Moderate doping leads to high performance of semiconductor/insulator polymer blend transistors," Nature Communications, Macmillan Publishers Limited, Mar. 12, 2013, 8 pp.

Mabeck et al., "Chemical and biological sensors based on organic thin-film transistors," Analytical and Bioanalytical Chemistry, Review, Aug. 4, 2005, 11 pp.

Patterson et al., "Electrochemical real-time nucleic acid amplification: towards point-of-care quantification of pathogens," Trends in Biotechnology, vol. 31, No. 12, Dec. 2013, 9 pp.

Rusu et al., Surface Dipoles and Work Functions of Alkylthiolates and Fluorinated Alkylthiolates on Au(111), The Journal of Physical Chemistry, Oct. 12, 2006, 24 pp.

Friend et al., "Using laser Doppler vibrometry to measure capillary surface waves on fluid-fluidinterfaces," Biomicrofluidics, vol. 4, Issue 2, Mar. 15, 2010, 5 pp.

Examination Report from counterpart European Application No. 15753592.3, dated Apr. 23, 2018, 4 pp.

* cited by examiner

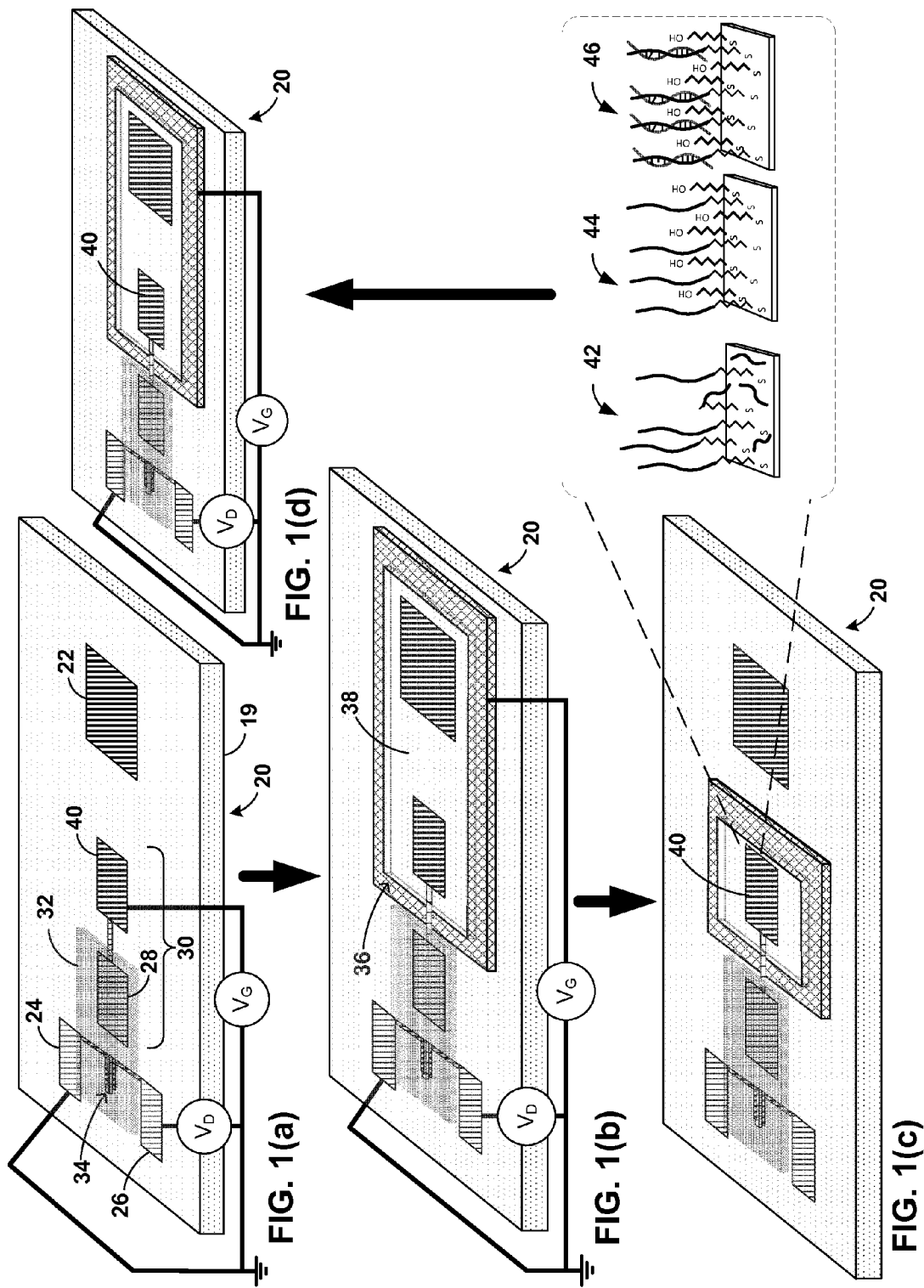

FIG. 22

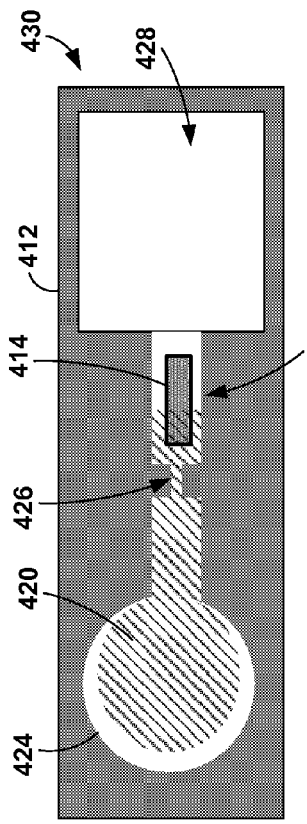
FIG. 25(b)
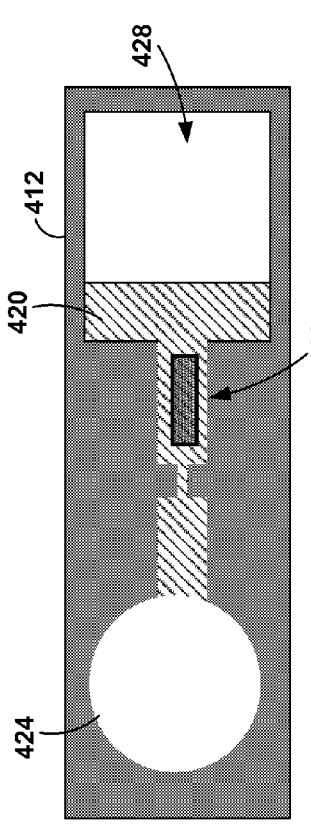
FIG. 25(d)
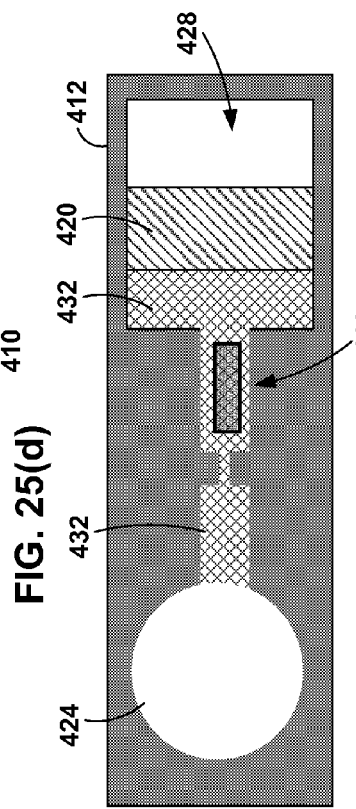
FIG. 25(f)
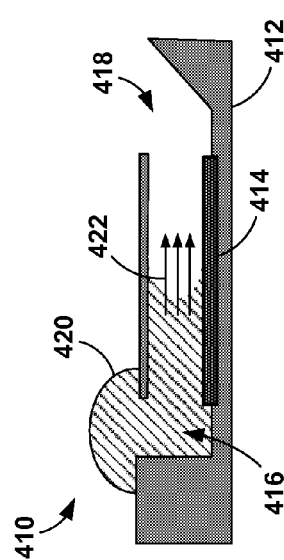
FIG. 25(a)
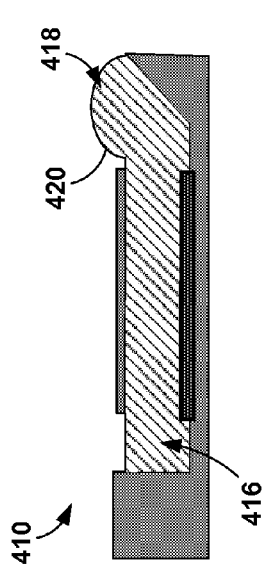
FIG. 25(c)
FIG. 25(e)

ELECTROLYTE-GATED TRANSISTORS FOR DETECTION OF MOLECULES

This application is a national stage application, under 35 U.S.C. § 371, of copending PCT Application No. PCT/US2015/045108 filed on Aug. 13, 2015, which claims priority to U.S. Provisional Patent Application No. 62/037,352 by White et al., filed on Aug. 14, 2014 and entitled "ELECTROLYTE-GATED TRANSISTORS FOR ELECTRONIC BIOSENSING," and U.S. Provisional Patent Application No. 62/202,477 by White et al., filed on Aug. 7, 2015 and entitled "ELECTROLYTE-GATED TRANSISTORS FOR DETECTION OF MOLECULES."

TECHNICAL FIELD

This disclosure relates to detecting molecules using electrolyte-gated devices.

BACKGROUND

Rapid and portable devices for the detection of molecules continue to be of interest for use in biothreat detection, point-of-care diagnostics, and other applications involving the detection of a target molecule. Some DNA detection methods include fluorescent labeling to determine whether a target portion of DNA is present in a sample. Other available DNA detection devices use electronic, colorimetric, or electrochemical sensing mechanisms. These approaches may avoid the use of fluorescent labels.

SUMMARY

This disclosure describes example methods, devices, and systems that generally include floating-gate transistors (FGTs) with electrolyte dielectrics for the detection of target molecules (e.g., molecules having a target chemical composition) in an analyte solution. In some examples, the target molecule to be detected may be a nucleic acid having a particular nucleotide sequence, such as a molecule of DNA or RNA. In other examples, the target molecule to be detected may be either a polypeptide having a particular amino acid sequence or constituting a particular protein. Example devices herein may achieve the electronic detection of target molecules by measuring changes in an electrical property, e.g., semiconductor conductance or electrical current, and outputting an indication of the measured electrical property as a result of whether or not the target molecule was present in the sample tested by the device. The electrical property may be measured at a drain electrode of the device, for example. Example devices disclosed herein also may achieve molecule detection and output of detection results without the labeling of target molecules or the optical detection of signals resulting from such labeling.

In one example, a device includes a semiconductor, an ionic conducting electronic insulator coupled to the semiconductor, a floating gate electrode comprising a first portion and a second portion, the first portion being coupled to the semiconductor via the ionic conducting electronic insulator, an aqueous buffer, and a primary gate electrode coupled to the second portion of the floating gate electrode via the aqueous buffer.

In another example, a system for detecting a molecule having a target chemical composition includes a semiconductor, an ionic conducting electronic insulator coupled to the semiconductor, a floating gate electrode comprising a first portion and a second portion, the first portion being coupled to the semiconductor via the ionic conducting electronic insulator, an aqueous buffer, a primary gate electrode coupled to the second portion of the floating gate electrode via the aqueous buffer, and one or more circuits configured to measure an electrical property based on a voltage change over the ionic conducting electronic insulator, and output an indication of the electrical property.

In one example, a method for detecting a molecule comprising a target chemical composition includes applying a voltage to a primary gate electrode of a device, the device including a source electrode and a drain electrode, the source electrode and the drain electrode being coupled to a semiconductor, an ionic conducting electronic insulator coupled to the semiconductor, a floating gate electrode comprising a first portion and a second portion, the first portion being coupled to the semiconductor via the ionic conducting electronic insulator, and an aqueous buffer, wherein the primary gate electrode is coupled to the second portion of the floating gate electrode via the aqueous buffer, measuring an electrical property at the drain electrode; and determining, based on the measured electrical property, whether the target chemical composition of the molecule is present within the aqueous buffer, and outputting an indication of the determination.

BRIEF DESCRIPTION OF DRAWINGS

FIGS. 1A-1D are schematic side elevation views of an example device, which includes a floating-gate electrolyte-gated transistor (EGT), as disclosed herein.

FIGS. 22 and 23 are graphs illustrating example experimental results of voltages measured in response to various target- and non-target compounds.

FIGS. 25A-25F are conceptual illustrations of an example device that uses capillary-driven flow to react a sample with the surface of a floating gate electrode.

DETAILED DESCRIPTION

Figure 2A:
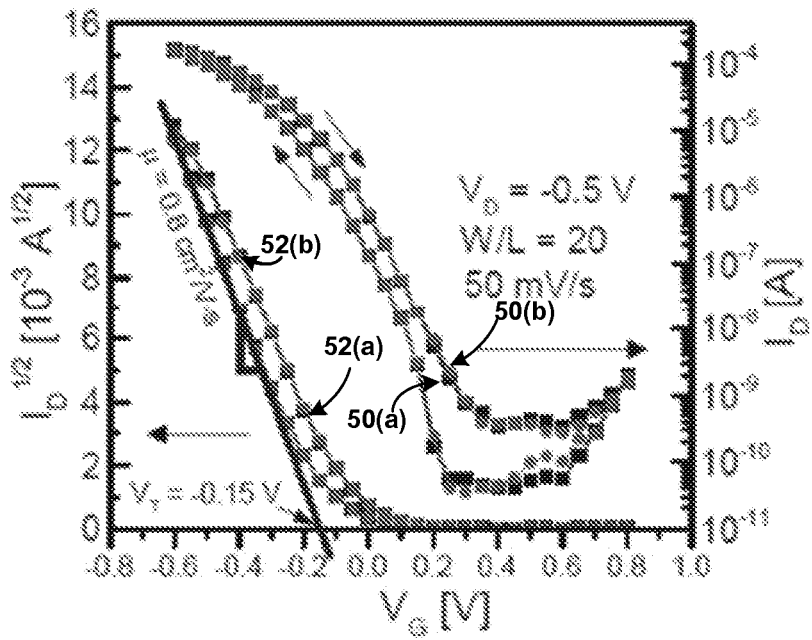
FIGS. 2A and 2B are graphs illustrating electrical principles associated with the device of FIGS. 1A-1D.

Examples described herein may implement a potentiometric approach to label-free molecule detection using electrolytes or ionic solutions capacitatively coupled to an organic semiconductor to form an electrolyte-gated transistor (EGT) having a floating-gate electrode architecture. In one example, the EGT may be based on poly(3-hexylthiophene) and an ionic conducting insulator serve as a transducer for surface chemisorption of molecules having a target chemical composition. In some examples, the EGT can use a floating gate electrode functionalized with a self-assembled monolayer (SAM) of molecules, wherein the potential of the EGT is determined both by capacitive coupling with a primary, addressable gate electrode and by the presence of adsorbed molecules. When target molecules encounter probe molecules chemisorbed at the floating gate electrode, the hybridization or binding of probe molecules with target molecules offsets the primary gate voltage experienced by the organic semiconductor; the offset being directly measurable and quantitatively related to the number and density of chemisorbed probe molecules. The detection device, system, and method of some examples can be adapted to a variety of molecules of interest (e.g., DNA, RNA, proteins, etc.) and integrated into a microfluidic system for field applications of molecule detection devices.

By using an EGT coupled to a microfluidic reservoir in a detection scheme, example devices may provide relatively increased signal gain, thereby allowing direct electronic readout of DNA hybridization or adsorption of another target molecule to a selected affinity reagent (e.g., a reagent portion of a probe that is selected for its affinity to a target chemical composition of a target molecule) of a probe. As with some example field-effect transistors (FETs), the current ($I_D$) through the semiconducting channel of an EGT is a strong function of the voltage applied to the drain electrode ($V_D$) and the voltage at a capacitively coupled gate electrode ($V_G$). For p-type EGTs, the current is low (or the device is OFF) when $V_G > V_T$ (where $V_T$ is the threshold voltage); but, when $V_G - V_T \approx V_D$, the current follows the saturation behavior:

$$I_D = \frac{W}{2L}\mu C_i (V_G - V_T)^2 \quad (1)$$

where W and L are the width and length of the semiconductor channel, $\mu$ is the carrier mobility in the semiconductor, and $C_i$ is the specific capacitance of the electrolyte gate-insulator. EGTs are well suited for potentiometric molecule detection because a large value of $C_i$ (on the order of 10 µF/cm) may be associated with an electrolyte gate-insulator. By virtue of a large small changes in $V_T$, which may occur in response to chemisorption on the floating gate electrode, can result in significant and easily detectable changes in $I_D$. An acute sensitivity of molecule-detection devices to small changes in $V_T$ can provide advantages when, as is common, relatively small quantities of nucleic acids or other molecules are present in a sample to be analyzed.

The performance of molecule-detection devices that employ EGTs may depend on the materials from which various device components are fabricated. For example, the composition of the dielectrics that insulate one or both sides (or surfaces) of the floating gate may be solid or aqueous. In some instances, EGT-based molecule-detection devices may include floating gates electrodes that employ solid dielectrics having relatively low capacitances; however, the use of low-capacitance dielectrics may limit the available change in semiconductor conductance for a given $V_T$ shift arising from capture of the target molecule. As a consequence of limited change in semiconductor conductance, such devices exhibit relatively lower sensitivity to target molecules. In some example devices described herein, both sides (or surfaces) of the floating gate electrode may be insulated by aqueous electrolyte dielectrics selected to have relatively high capacitance, which thereby causes such devices to exhibit greater sensitivity to target molecules than materials having lower capacitances. Also, in some examples described herein, the performance of such devices may further be improved by the functionalization of the floating gate electrode with SAMs. SAMs may lower the work function (i.e., the energy required to move an electron) of the floating gate electrode and improve the sensitivity of such devices.

Some example devices described herein may implement a floating-gate electrode into a high capacitance (or low-voltage) EGT. This sensor architecture of various examples can provide pronounced sensitivity due to the extremely large EGT transconductance (e.g., $\frac{dI_D}{dV_G}$ taken from Equation (1)), because such sensor architecture provides large changes in semiconductor conductance for a given potentiometric signal ($V_T$ shift). Additionally, the sensor architecture of some examples allows for low operating voltages that make such devices amenable to a variety of printable, lab-on-a-flexible-substrate schemes. Moreover, the architecture of some examples described herein allows for a floating gate design that separates the molecular capture interface from the electronically controlled electrode. This separation may help to avoid exposure of the semiconductor to aqueous analyte solutions and the resultant degradation of the semiconductor that would otherwise occur with such exposure.

In some types of devices used to detect molecules, devices may employ fluorescent labeling of analyte molecules and subsequent optical detection of fluorescence within the device. In other examples, such devices may rely on electrochemical responses, wherein an electric current is employed to cause a chemical change. Both of these types of devices, in addition to requiring relatively high operating expenses, complicate both sample preparation and signal detection. Furthermore, such example devices lack direct electronic indications of detection, and, as such, are not readily interfaced with other electronic or computing devices. As described herein, devices that utilize an EGT may provide direct electronic indications of detection without labeling of the molecules (e.g., label-free detection), thus simplifying sample preparation and signal detection, while avoiding the use of analyte labels, optical detection, and electrochemical responses. Devices described herein using an EGT may provide sensitivity and selectivity for target molecules. Detection may also be implemented in portable devices, require minimal sample preparation, and fast detection output.

Although some examples herein pertain to the detection of nucleic acids (e.g., device 20), it should be noted that the following examples may also pertain to the detection of other types of target chemical compositions using similar principles. Therefore, the examples described herein may be used to detect a variety of different types of molecules, small and large, and are not limited to the detection of nucleic acids or to any particular category of target chemical composition.

FIGS. 1A-1D include schematic side elevation views of an example device 20. As shown in FIG. 1A, device 20 includes a substrate 19, primary gate electrode 22, floating gate electrode 30, semiconductor 34, source electrode 24, and drain electrode 26. In some examples, floating gate electrode 30 includes a first portion 28 and a second portion 40. First portion 28 may be coupled to semiconductor 34 via an ionic conducting electronic insulator 32, while second portion 40 may be coupled to primary gate 22 via an aqueous electrolyte buffer 38 (as shown in FIG. 1B. Aqueous electrolyte buffer 38 may be contained within detection reservoir 36 of device 20. In this manner, detection reservoir 36 is configured to contain an aqueous buffer such as buffer 38 and a sample that may include a target molecule. In some examples, semiconductor 34 may be connected to source electrode 24 and drain electrode 26. Collectively, semiconductor 34, ionic conducting electronic insulator 32, floating gate electrode 30, aqueous buffer 38, and primary gate electrode 22 may be described as, or including, a floating gate transistor in operation.

Semiconductor 34 may be constructed of an organic material, such as poly(3-hexylthiophene) (P3HT). During fabrication of device 20, semiconductor 34 may be printed from solution onto a silicon wafer (e.g., substrate 19) in a configuration allowing coupling of semiconductor 34 to source electrode 24 and drain electrode 26. In some examples, electrons may be removed from the overlapping p-orbitals of the P3HT material ("p-doping"), resulting in modulation of the electrical properties of semiconductor 34 and contributing to the p-type configuration of the EGT described above.

As shown in FIGS. 1A-1D, ionic conducting electronic insulator 32 may be printed, in sequence with semiconductor 34, onto a silicon wafer during fabrication of device 20 such that ionic conducting electronic insulator 32 and semiconductor 34 are positioned in a planar, side-gated geometry. In some examples, ionic conducting insulator 32 may be composed of a mixture of polystyrene-b-methylmethacrylate-styrene (SMS) and 1-ethylmethyl imidazolium bis(trifluoromethyl)sulfonylimide (EMIM/TFSI) at 1:9 by weight. While device 20 is in use, ionic conducting electronic insulator 32 may function as one or more electrolyte dielectrics, insulating one or more sides (or surfaces) of floating gate electrode 30 from semiconductor 34 and providing relatively high capacitance to device 20.

Floating gate electrode 30 may consist of two separate portions, or arms, in an example device as described herein. Both first portion 28 and second portion 40 may be printed, in a manner similar to that used for printing semiconductor 34 and ionic conducting electronic insulator 32, onto a silicon wafer during fabrication of device 20. In some examples, first portion 28 and second portion 40 may be printed from a metallic solution, such as an Au solution in one example. In floating gate electrode 30, first portion 28 may be coupled to semiconductor 34 via direct contact with ionic conducting insulator 32. Second portion 40, which may include an analyte capture surface to which analyte solution is applied, may be positioned adjacent to detection reservoir 36 and in contact with aqueous buffer 38. This configuration allows for the transmission of current from semiconductor 34 to second portion 40 in a manner that avoids contact between the analyte capture interface of second portion 40 and electrodes under direct electric control.

In some examples, second portion 40 of floating gate 30 may have a surface that is functionalized with self-assembled monolayers (SAMs), thereby altering the work function of device 20 (e.g., raising or lowering the amount of energy required to move an electron). Such SAMs may consist of molecules such as 6-mercapto-1-hexanol (MCH) or 3,3,4,4,5,5,6,6-nonaflouro-1-hexanol (NFH), as some examples, diluted in a solution of distilled water or ethanol, selectively flowed over a side of floating gate 30, and allowed to absorb to a surface of floating gate 30. The functionalization of floating gate 30 with SAMs may further increase the sensitivity and improve overall performance of device 20, as described in FIG. 16.

In some examples, aqueous electrolyte buffer 38 couples second portion 40 and primary gate 22. Aqueous buffer 38, which may be composed of a phosphate buffered saline (PBS) solution, for example, may function as an electrolyte dielectric capable of insulating second portion 40 and transmitting voltage from second portion 40 to primary gate electrode 22.

Primary gate electrode 22 also may be printed from a metallic solution, such as an Au solution in one example, onto a silicon wafer during fabrication of device 20 in a manner similar to the manner described above for the printing of semiconductor 34 and primary gate 30. As shown in FIGS. 1B and 1D, in some examples, primary gate 22 controls floating gate 30 via capacitative coupling with floating gate 30 via aqueous electrolyte buffer 38.

The operation of device 20 may be tested in a side-gated architecture prior to use of device 20 in molecule-detection applications. As shown in FIG. 1A, the application of a voltage directly to floating gate electrode 30 (which in such a case electrode 30 is no longer floating), modulates the conductance of the semiconductor 34, which can be measured directly as a change in drain current at drain electrode 26, as according to Equation (1). These measurements can be output, for example displayed to a user, or output in some other fashion by for example audible alerts. Following testing of device 20 in the configuration shown in FIG. 1A, device 20 may then be used in the floating-gate architecture illustrated in FIGS. 1B and 1D, wherein voltage is not applied directly to floating gate 30, but instead applied directly to primary gate 22.

As shown in FIG. 1C, the surface of second portion 40 may be chemically bound with probe molecules. Probe molecules, alternatively referred to as or including affinity reagents, may include molecules (e.g., nucleic acids, nucleic acid analogs, aptamers, polypeptides, proteins, and antibodies, etc.) for which the molecule targeted to be detected will have a chemical affinity. These molecules to be detected may alternatively be referred to as having a target chemical composition. In this manner, an affinity regent being included in a probe may be selected for its affinity to the target chemical composition so that the target chemical composition, and its molecule, can be detected by the device and systems described herein. In one example, probe molecules may partially consist of oligonucleotides having a complementary sequence to the target nucleic acid. In such a case, the probe oligonucleotide may be modified with a molecule, such as a thiol functional group, having a chemical affinity for gold atoms situated at the surface of second portion 40 and bound thereto. In other examples, the probe molecules may consist of nucleic acid analogs, polypeptides, antibodies, or other proteins, in each case the probe molecules selected or configured to have chemical affinity for the target chemical composition. Similarly to the example wherein the probe molecule consists of an oligonucleotide, other classes of probe molecules also may be modified with a molecule having an affinity for gold atoms, or any other material at the surface of second portion 40, situated at the surface of second portion 40 and bound thereto. In this manner, probe molecules may be tethered at one end to the surface of second portion 40 while remaining free to interact with a target chemical composition at another end.

Also as shown in the example of FIG. 1C, the surface of the second portion 40 may be chemically bound with blocking molecules while simultaneously being chemically bound with probe molecules. Blocking molecules, for example, molecules of 6-mercapto-1-hexanol (MCH) having a chemical formula of $HS(CH_2)_6OH$, may be applied to second portion 40 after, or simultaneously with, second portion 40 has been reacted with probe molecules. Analyte samples, especially those of biological origin, may contain many molecules not having the target chemical composition. However, some non-target molecules within an analyte sample may, despite failing to react with the probe molecules, nonetheless react directly with the surface of second portion 40 in a manner that may cause a change in $V_T$, or otherwise affect the electrical properties of the floating gate electrode 30. In addition, unreactive probe molecules may cause a change in $V_T$. Because a change in $V_T$ caused by non-target molecules or unreactive probe molecules would interfere with the detection of the target chemical composition, it may be desirable to displace non-target analyte molecules from the surface of second portion 40, and also prevent further non-specific adsorption, prior to performing an analysis of the analyte sample. Blocking molecules may thus achieve this function due to the blocking molecules having a relatively greater chemical affinity for second portion 40 than non-target analyte molecules. The blocking molecules may be collectively referred to as a blocking layer, or passivation layer, of molecules, even though the blocking molecules and probe molecules may both be bound to second portion 40 of the floating gate electrode.

In other examples, some of the probe molecules may not appropriately bind (small pieces laying on the surface) to the surface of the second portion 40 as shown in surface 42. In surface 44, blocking agents have displaced the inappropriately reacted probe molecules. In surface 46, probe molecules have bound to target molecules. In other examples, the blocking molecules may be added at the same time as the test sample.

To render example device 20 more convenient and commercially viable, device 20 may be coupled to one or more circuits. Such circuits may be configured to provide voltage to device 20, measure a current or voltage (e.g., an electrical property) at the drain electrode (e.g., $V_D$) from primary gate electrode 22, or subsequently output an indication of the voltage, among other configurations. Voltages applied to the drain electrode 26 and primary electrode 22 may vary based on properties of device 20 (e.g., size of components and materials used), properties of the probe molecules and target chemical compositions, and properties of the analyte and/or dielectric materials.

FIG. 2A is a graph illustrating that the testing of device 20 in two different geometries (FIG. 1A vs FIG. 1B) does not alter the $I_D$-$V_G$ characteristics of the side-gate EGT, a phenomenon resulting from the domination of the potential at the floating-gate electrode ($V_F$) by the primary gate electrode ($V_G$). In this figure, curves 50(a)-50(b) depict data on a logarithmic scale, and curves 52(a)-52(b) reproduce the same data on a linear scale.

FIG. 2A demonstrates that sweeping $V_G$ negatively turns the EGT ON (the source-drain hole current increases) whether device 20 is tested in the FIG. 1A or FIG. 1B configuration. This happens because the application of $V_G$ to primary gate electrode 22 equivalently biases floating gate electrode 30, $V_F$, due to capacitive coupling. FIG. 2A illustrates that that with no chemisorption of probe molecules on second portion 30, $V_T$ is independent of whether the gate bias is applied directly to floating gate 30 or to primary gate 22. In other words, the curves are approximately equal whether the voltage is applied to either floating gate 30 or primary gate 22. This phenomenon is illustrated by curves 50(a)-50(b) and 52(a)-52(b), wherein the configuration in which device 20 is tested does not alter the $I_D$-$V_G$ characteristics of the side-gated EGT. Specifically, curves 50(a) and 52(a) illustrate an increase in the source-drain hole current that occurs when device 20 is tested in the side-gated architecture of FIG. 1A, whereas curves 50(b) and 52(b) illustrate a similar increase in the source-drain hole current that occurs when device 20 is tested in the floating-gate architecture of FIG. 1B.

Figure 2B:
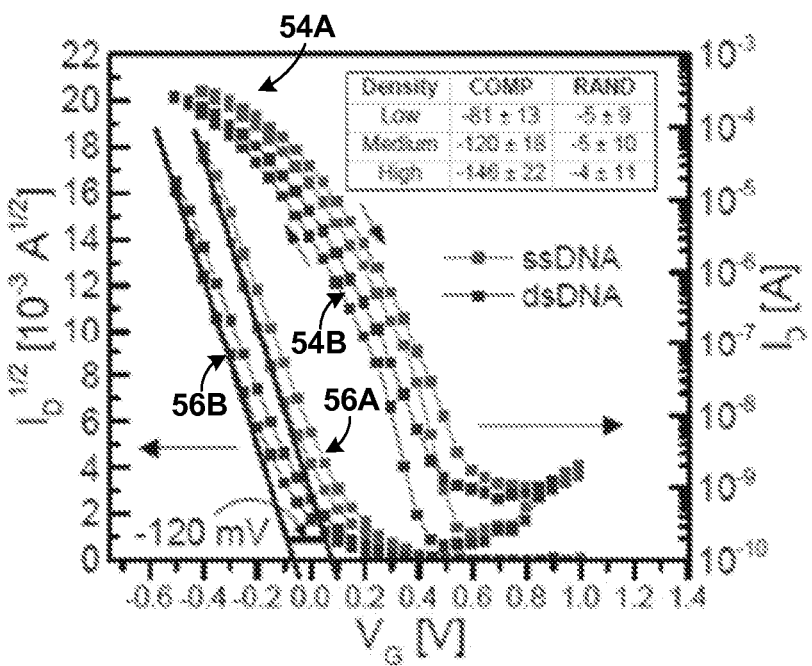

FIG. 2B demonstrates that the formation of double stranded DNA (dsDNA) on the functionalized floating gate electrode results in a significant −120 mV shift in the $I_D$–$V_G$ characteristic of the EGT. This occurrence is illustrated by curves 54B and 56B, obtained following the formation of dsDNA, which have shifted relative to the respective curves (i.e., curves 54A and 56A) obtained from single stranded DNA (ssDNA). In this case, the FIG. 1D configuration (the sensor mode) was employed for both traces.

It will be appreciated upon examination of FIG. 2B that the hybridization of dsDNA on floating gate 30 results in a significant −120 mV shift in the $I_D$–$V_G$ characteristic of device 20 when device 20 is re-tested in the FIG. 1D configuration. The size of the voltage shift is a function of ssDNA surface density at the surface of second arm 40. In some examples, a moderate probe density (7 pmol/cm$^2$) can be used, thereby generating larger signals (as illustrated by the inset of FIG. 2B) signal (inset FIG. 2B) while avoiding non-idealities associated with densely packed probe molecules.

Although the example in FIG. 2B illustrates transfer curves resulting from the chemisorption of an ssDNA probe and the formation of a dsDNA complex resulting from hybridization of the target chemical composition with a probe molecule, a similar principle would be illustrated where device 20 is used to detect chemical compositions including molecules other than nucleic acids.

The relationship between $V_G$ and $V_F$ in this scenario is derived and described below with reference to FIGS. 3A-3B and FIGS. 4A-4B. The schematic of device 20 (e.g., a floating-gate EGT) in FIG. 3A can be approximated as the equivalent circuit shown in FIG. 3B, where the capacitors represent electric double layers and the nodes represent electrodes or electrolyte bulks. FIGS. 4A and 4B are alternative equivalent circuit models used in the derivation.

Figure 3A:
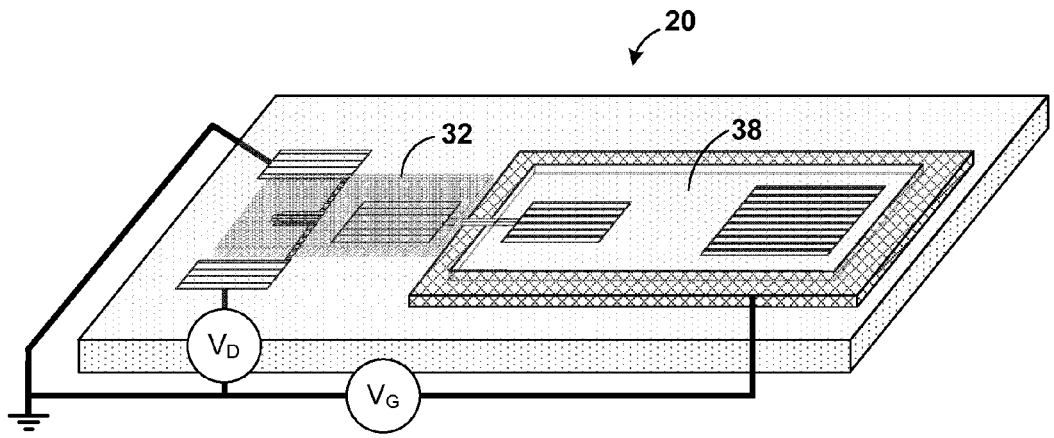
FIG. 3A is a schematic side elevations of the EGT of FIG. 1.
Figure 3B:
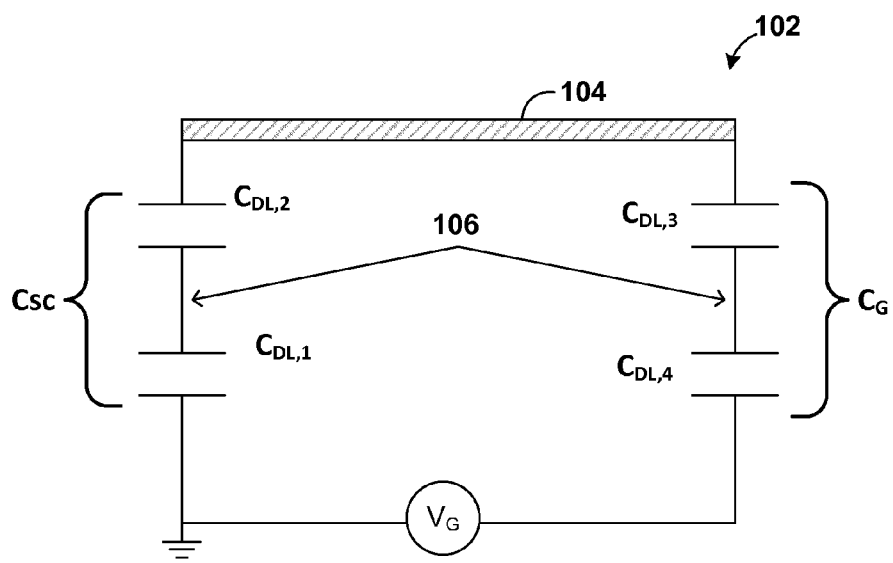
FIG. 3B is a conceptual drawing of an example circuit model of the sensing device of FIGS. 1A-1D.
Figure 4A:
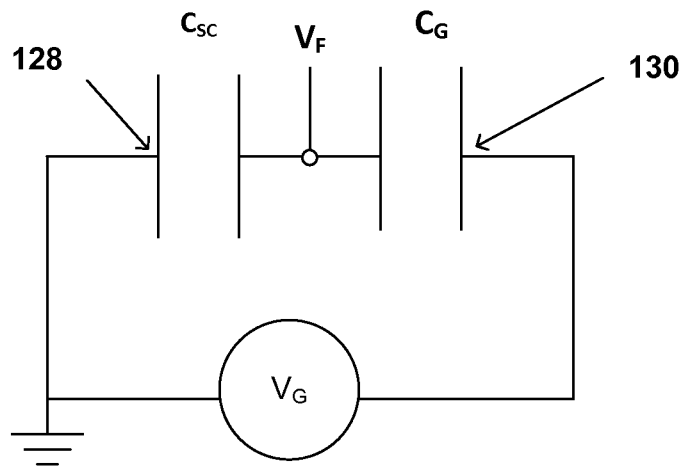
FIGS. 4A and 4B are conceptual drawings of example equivalent circuit models in accordance with the device of FIGS. 1A-1D.
Figure 4B:
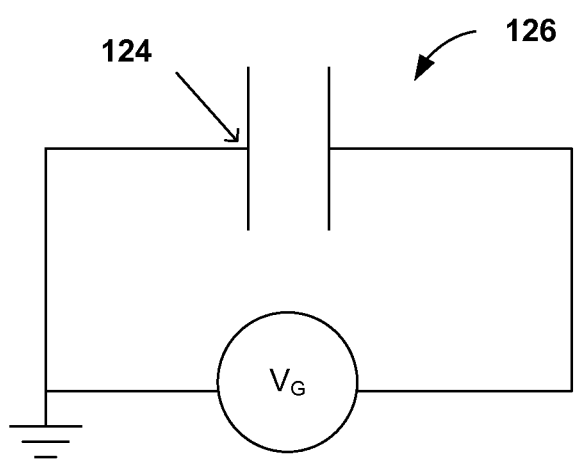

The equivalent circuit in FIG. 3B represents the floating gate EGT in FIG. 3A under the following assumptions: (1) No gate current, (2) semiconductor 34 is held at ground, and (3) constant capacitances. The double-layer capacitances ($C_{DL}$) can be combined using $1/C = 1/C_{DL,1} + 1/C_{DL,2}$ to define the total capacitance between floating gate electrode 30 and semiconductor 34 $C_{SC}$) and between floating gate electrode 30 and primary gate electrode 22 ($C_G$). In FIG. 4B, the total capacitance, $C_{Total}$, can be defined in a similar way with $C_{SC}$ and $C_G$ and used to define the total charge, $Q_{Total}$, separated in the device. When separating the total capacitance into its constituents ($C_{SC}$ and $C_G$) in FIG. 4A, it should be noted that this total charge is also separated on each capacitor when they are placed in series, $Q_F$ and $Q_G$. Equating the charge on $C_{SC}$ with the total charge in FIG. 4B gives:

$$Q_F = Q_{Total} \tag{2}$$

Substituting the definition of capacitance (Q=CV) and $1/C_{Total} = 1/C_{SC} + 1/C_G$ gives $$C_{SC}V_F = \frac{C_{SG}C_G}{C_{SC}+C_G}V_G \tag{3}$$

Solving for $V_F$ in terms of $V_G$, $$V_F = \frac{C_G}{C_{SC}+C_G}V_G \tag{4}$$

By examination of Equation (4), it will be appreciated that the floating gate potential ($V_F$) follows the primary gate potential ($V_G$) if $C_G \gg C_{SC}$ (e.g., primary gate electrode 22 dominates the capacitive coupling). FIG. 4A illustrates the representative circuit of the EGT with the capacitances of the semiconductor at node 128 and the capacitance of the gate at node 130 are in series on either side of the floating gate electrode. Therefore, these capacitances in FIG. 4A can be solved to result in an equivalent circuit of FIG. 4B having a single capacitance 126 at node 124.

To operate the sensor of device 20, in various examples, device 20 can be configured according to FIG. 1D by covering the functionalized second portion 40 of floating gate electrode 30 and primary gate electrode 22 with aqueous buffer 38. The resulting transfer curve, which indicates a voltage at primary gate electrode 22, is shifted positively from curves 50 and 52 in FIG. 2A due to the formation of gold—thiol bonds, and can be taken as the background signal as will be discussed later herein with respect to FIGS. 6A-6D. Where the target chemical composition is a DNA or RNA molecule, exposure of complementary DNA or RNA to an immobilized probe oligonucleotide chemisorbed to the surface of second arm 40, according to the configuration shown in FIG. 1C, will result in the hybridization of dsDNA or dsRNA on floating gate 30 as confirmed by fluorescence microscopy as discussed later herein with respect FIG. 8. Where the target chemical composition is a molecule not consisting of nucleic acid, a similar shift in transfer curve will occur upon chemisorption of the target composition molecule to the probe molecule. The operation of device 20 can be understood by recognizing that the selective chemisorption of various probe molecules, such as probe molecules consisting at least partially of DNA, to the interface of floating gate 30 and aqueous buffer 38, may create a voltage offset between floating gate 30 and primary gate 22. In some examples, the chemisorption of probe molecules alters the effective double-layer potential created at the interface of floating gate 30 and aqueous buffer 38, such that a more negative $V_G$ on primary gate 22 may be needed to turn the EGT ON, as observed in FIG. 2B. Mathematically, examples account for this voltage offset by treating this voltage offset as a correction to the threshold voltage for the $I_D$–$V_G$ characteristics in the saturation regime, $$I_D = \frac{W}{2L}\mu C_i(V_G - [V_T + \Delta V])^2 \tag{5}$$

The sensitivity of the floating-gate EGT of various examples can be demonstrated by varying the concentration of ssDNA exposed to second arm 40 from 10 nM to 10 μM. Measurements can be taken at steady-state by increasing the hybridization time for lower concentrations ($\tau \sim 1/k_{on}C_{DNA}$, $k_{on} \sim 10^4$ M$^{-1}$ s$^{-1}$).

Figure 5A:
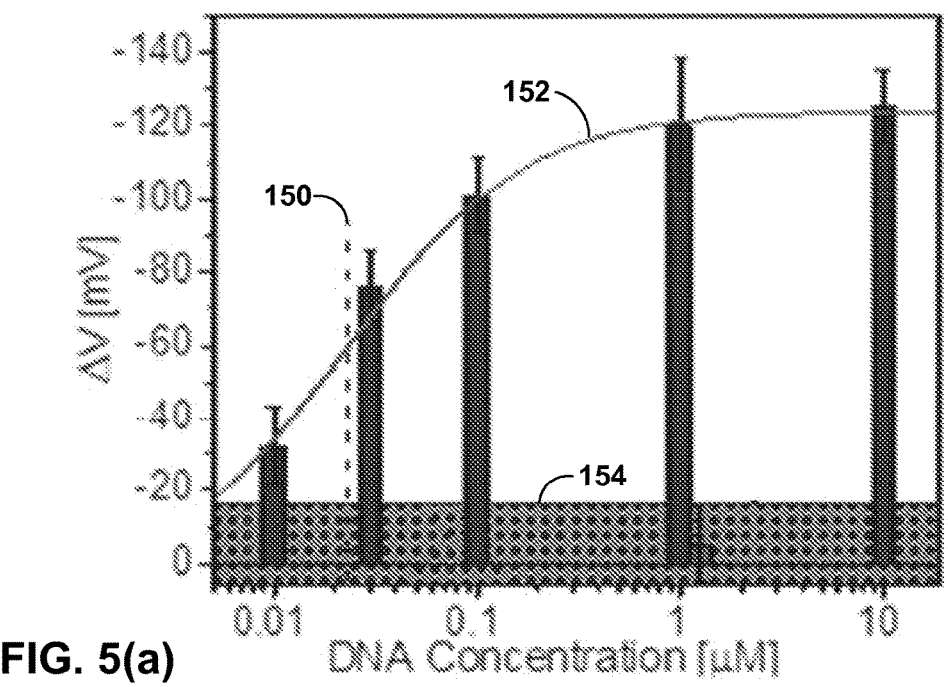
FIGS. 5A and 5B are graphs illustrating example test results for the sensitivity and selectivity of the device of FIGS. 1A-1D.

FIG. 5A illustrates a graph depicting an example sensitivity test, which show that electrical signal 152 is saturated at high concentration (≥1 μM) of DNA, but that electrical signal 152 steadily declines for lower concentrations of DNA. The data can be fit by a Langmuir isotherm ($\upsilon = C_{DNA}/(C_{DNA}+K_D)$) with $K_D = 25$ nM (shown by dotted line 150) by assuming the ΔV decreases due to the smaller fraction of probes chemisorbed at the surface of second arm 40 being hybridized to dsDNA ($\upsilon = \Delta V/\Delta V_0$). The limit of detection for this configuration will be 10 nM, assuming background level 154 is equal to the signal from adding random DNA (<20 mV). The intrinsic background can be caused by a combination of EGT instability, non-specific adsorption of DNA, and drifting potentials of primary gate 22.

Figure 5B:
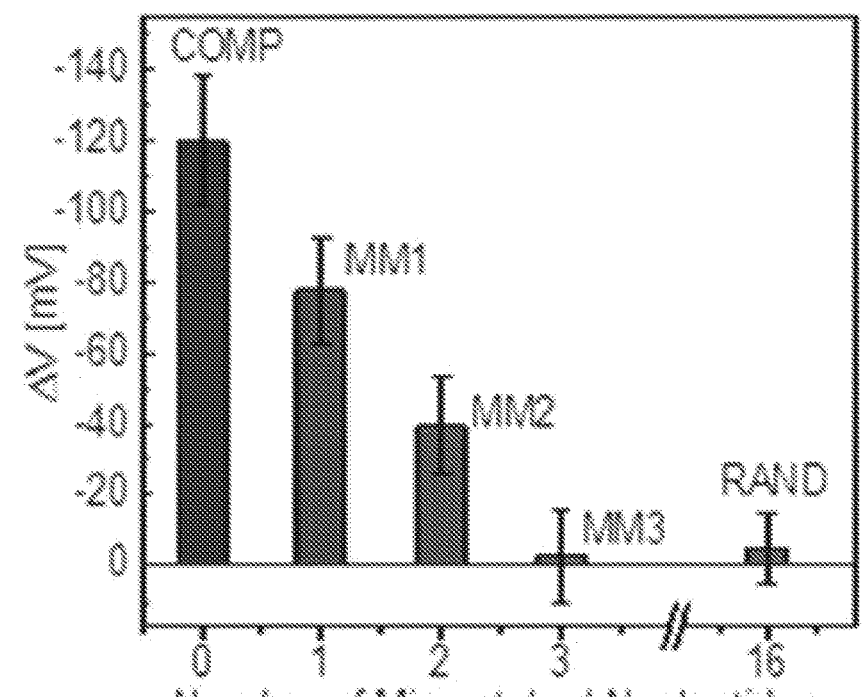

The selectivity of device 20 can, in various examples, be measured by varying the sequence of target ssDNA in solution. The number of mismatched base pairs can be increased until the signal is indistinguishable from a random sequence. FIG. 5B demonstrates that there is a measurable difference in $V_T$ for a sequence with only one mismatched base pair (MM1). Also as demonstrated in FIG. 5B, sequences containing as few as three mismatched base pairs (MM3) exhibit responses indistinguishable from a fully random sequence (RAND).

Figure 10:
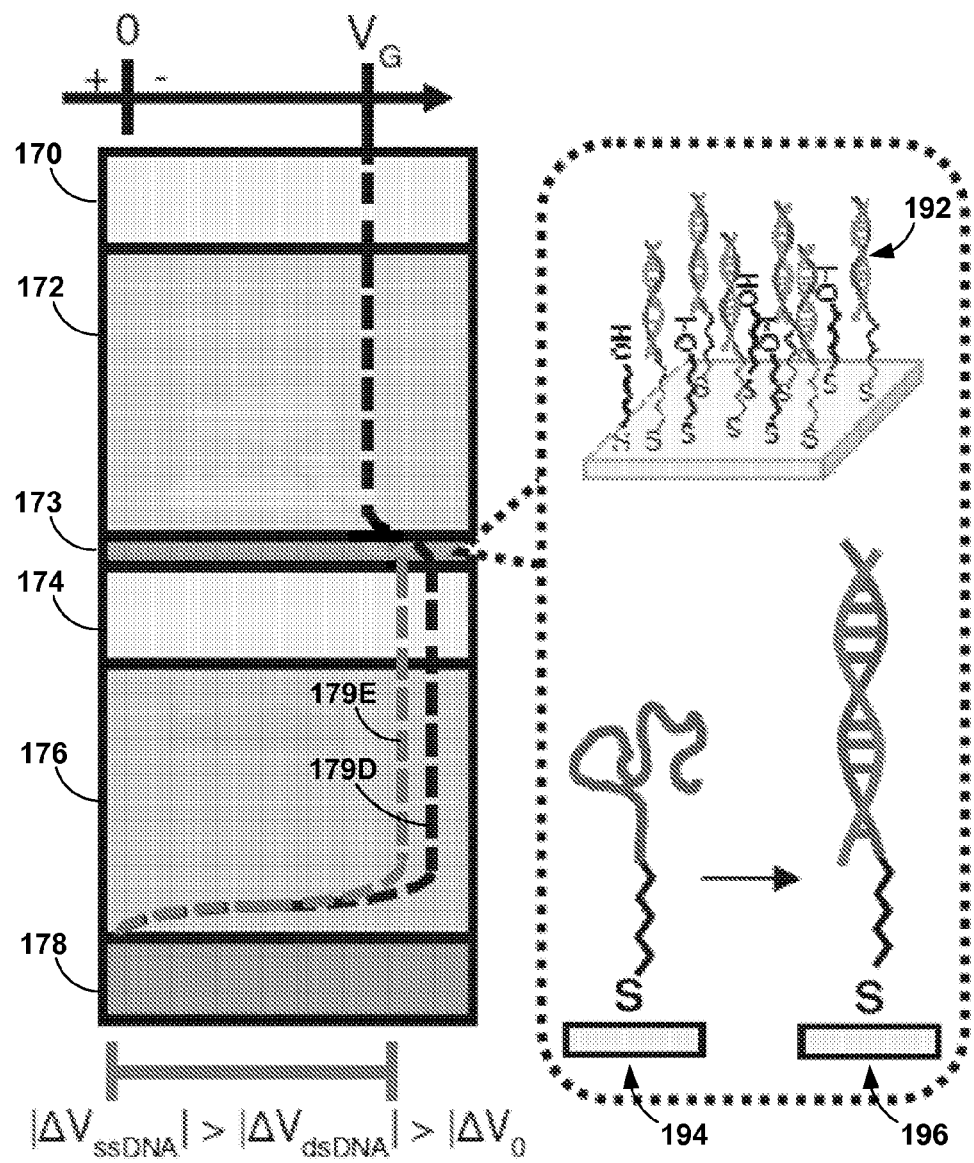
FIG. 10 is a conceptual illustration of the effect of DNA hybridization on a potential profile of the EGT of FIGS. 1A-1D.
Figure 12:
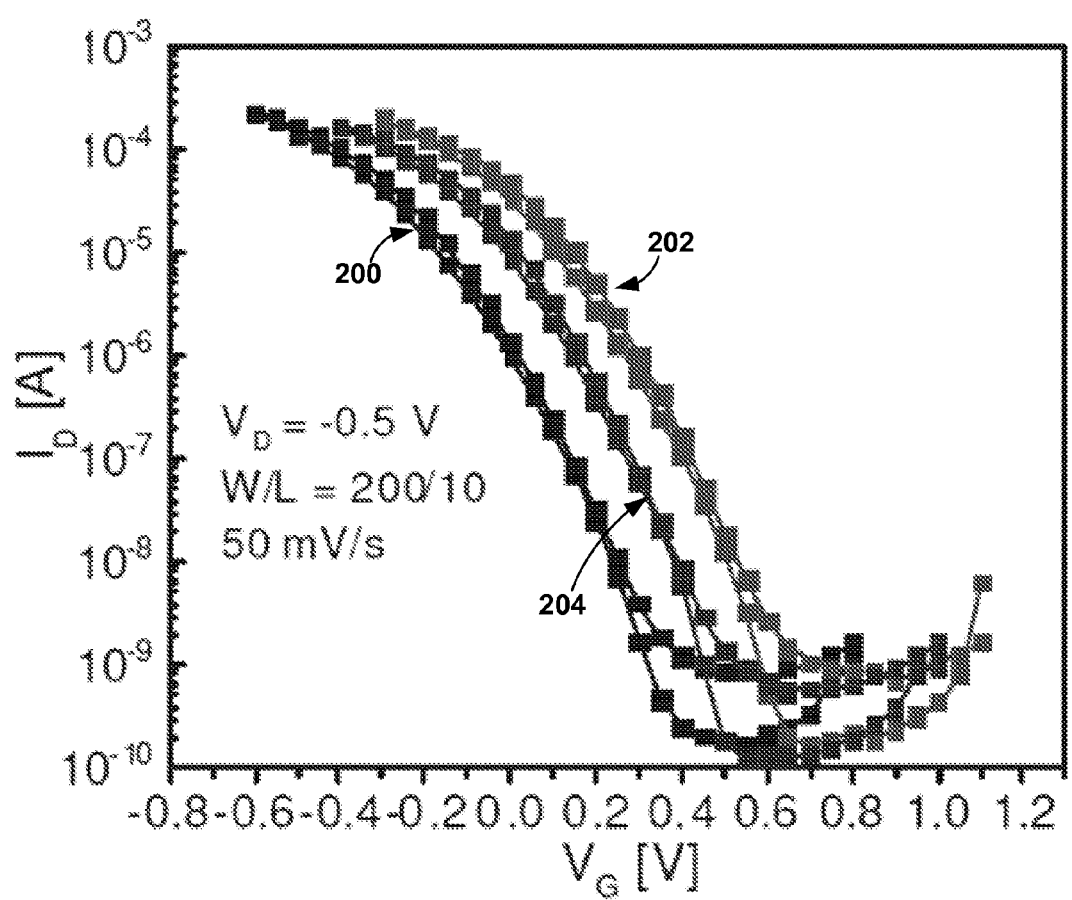
FIG. 12 is a graph illustrating the effects of ssDNA adsorption and dsDNA formation on the conductance of a floating gate of the EGT of FIGS. 1A-1D.

With reference to FIGS. 2B, 10, and 12, negative shifts in $V_T$ occur when ssDNA is hybridized to form dsDNA. This hybridization event brings about a number of changes in electrical properties of the immobilized molecule such as increased conductivity, polarizability, and negative charge. Available floating-gate transistors have differentiated between ssDNA and dsDNA by using the increase in negative charge on the floating gate to electrostatically shift the voltage at the coupled semiconductor ($\Delta V \approx Q_{DNA}/C$). However, applying this model to various examples of this disclosure predicts an increase in $I_D$ at a given $V_G$ in contrast to the result seen in FIG. 2B. If the negative charge at the interface of floating gate 30 and aqueous electrolyte 39 reflects at the interface of floating gate 30 and ionic conducting electrolyte insulator 32. Such a reflection of charge may negatively bias semiconductor 34, thereby increasing the conductivity of semiconductor 34. Importantly, one distinction between the design according to various examples of the present disclosure and other examples of molecular detection devices is the location of the analyte. In some examples, as described in further detail with regard to FIGS. 15A and 15B, an analyte solution may be located at an interface consisting of an integral component of the device, such as semiconductor 34. In examples described herein, a preparation containing an analyte, such as a solution, may be located away from integral components of a device, such that the integral components are not subjected to degradation resulting from contact with the analyte preparation.

Some examples of label-free DNA sensing strategies cause DNA to bind to a metallic surface, such as a gold surface, and detect subsequent DNA hybridization as a voltage offset originating from the resulting lowered work function (i.e., the decrease in the amount of energy required to move an electron) of the metallic surface. The molecular origin of the observed change can be explained in terms of the altered surface potential resulting from the hybridization of an ssDNA probe with a target DNA sequence ($\Delta V \approx \mu DNAN/\varepsilon$, where $\mu$ is dipole of the DNA strand and N is the areal density). A combination of altered charge, dipole orientation, and dielectric permittivity between ssDNA and dsDNA result in the observed decrease in work function in experiments such example label-free DNA sensing strategies. In such examples, the functionalized electrode can be allowed to equilibrate with the reference because both electrodes are electronically connected (e.g., "not floating"). In contrast, floating gate electrode 30 of various examples described herein will not completely equilibrate with primary gate electrode 22.

Various examples can be described in terms of the potential profiles from primary gate 22 to semiconductor 34, because the measured $I_D$ (Equation (1)) is determined by a voltage drop at the interface of semiconductor 34 and ionic conducting electronic insulator 32. After chemisorption of ssDNA probes and blocking molecules, such as MCH molecules, the $V_T$ shifts positively from $V_T$ measurements taken before chemisorption, as described below with reference to FIGS. 7A-9. In some examples, the formation of Au—S bonds between gold atoms at the surface of floating gate electrode 30 and sulfur atoms of the thiol groups of the MCH molecules results in an immobilized dipole with the negative side oriented towards the electrode, because sulfur donates electron density to the metal. This scenario negatively biases floating gate 30 with respect to primary gate 22, thereby making semiconductor 34 more conductive at a given $V_G$. After hybridization of dsDNA, the $V_T$ shifts negatively, but remains shifted positively relative to the $V_T$ measurement taken before chemisorption. This can be rationalized in terms of an altered interfacial dipole between ssDNA and dsDNA and is described in more detail herein below with reference to FIGS. 10-12. On a molecular level, dsDNA carries more negative charge than ssDNA and is oriented more perpendicularly to the surface of device 20. This reorganization of charge is thought to cause an altered interfacial dipole at the interface of floating gate 30 and ionic conducting insulator 32, thereby giving rise to the observed shift in $V_T$. The magnitude of this voltage shift is proportional to the fraction of the surface of second arm 40 covered with dsDNA, which, as demonstrated in FIG. 5A, allows for improved quantitative analysis. Examples also exhibit a slight decrease of the interfacial capacitance between ssDNA and dsDNA, which, due to the reduced capacitive coupling between floating gate 30 and primary gate 22, may also contribute to the observed voltage shift ($C_G$ in FIGS. 3A-4A).

The pronounced selectivity to mismatched sequences demonstrated by device 20 may result from a combination effects; such as signal changes due to altered interfacial dipoles, capacitance, and the fraction of ssDNA probes reacted. On a molecular level, complexes formed between ssDNA probes and a mismatched DNA sequence carry the same nominal charge as specifically-formed complexes of dsDNA. However, the orientation and electric polarizability of a non-specifically formed complex can be diminished in relation to a specifically-formed complex. Thus, complexes formed from a non-specific interaction of an ssDNA probe with a mismatched DNA sequence may exhibit a relatively smaller change in interfacial dipole per strand than would be observed with a specifically-formed complex. Thus, non-specifically formed complexes ultimately result in a relatively smaller $V_T$ shift than do specifically formed complexes Additionally, non-specifically formed complexes may exhibit smaller equilibrium coverage on the floating gate, thereby diminishing the signal in to an extent similar to the diminished signal observed at lower concentrations of complementary DNA in FIG. 5A. The sensitivity to base mismatches depicted in FIG. 5B is a combination of the aforementioned effects and represent at least one feature or benefit of the label free, electronic approach to molecule detection described by some examples of this disclosure.

Implementing a floating-gate electrode into a low-voltage EGT allows hybridization or other molecular-complexing events at the surface of second arm 40 to be recorded as an altered conductivity of semiconductor 34. The design of device 20 can, in various examples, eliminate the need for labeling reagents, and also may provide improved electronic readout and selectivity. Additionally, the strategy employed by examples described herein may readily be multiplexed into an array of sensors that are connected with a microfluidic network. Some example devices described herein may provide enhanced limits of target chemical composition detection, and also may minimize the large amount of solution (100 µL) that in some examples may be used to fully functionalize the electrode. Examples described herein may achieve these results through optimization of the circuit design and microfluidic handling of a sample.

Figures 6A, 6B, 6C:
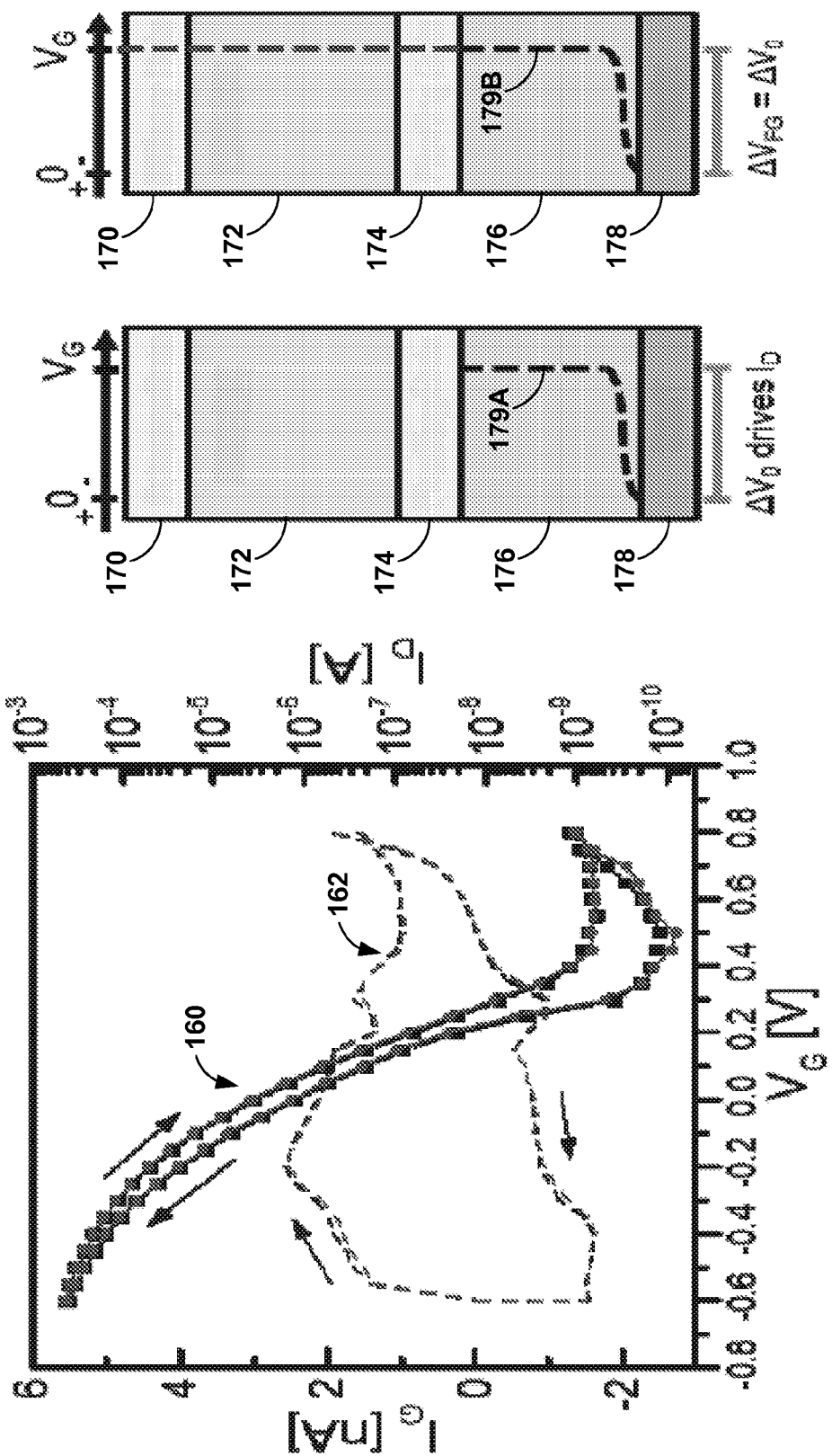
FIGS. 6A-6C are conceptual illustrations of example operations of the EGT of FIGS. 1A-1D.

FIGS. 6A-6C illustrate floating gate operation in accordance with some examples. The planar, side-gated architecture and electrolyte materials allow the device of various examples described earlier herein to be tested with and without a floating-gate. As shown in FIG. 6A, there is no observed difference in $I_D$-$V_G$ or $I_G$-$V_G$ characteristics between the example of FIGS. 1A and 1B. This can be attributed to the fact that curve 160 represents both sets of data, since the capacitance at the aqueous interfaces are much larger than the ion-gel interfaces ($C_G$>>$C_{SC}$). Therefore, curves 160 and 162 also show the data from both examples of FIGS. 1A and 1B.

FIGS. 6B and 6C are simplified representations of the potential through an example device (e.g., device 20) when such a device is tested in the two configurations illustrated in FIG. 1A and FIG. 1B. Specifically, the representation of FIG. 6B corresponds with the configuration of FIG. 1A, and the representation of FIG. 6C corresponds with the configuration of FIG. 1B. In the examples of FIG. 6B and FIG. 6C, device 20 may include semiconductor 178 (comprising an organic material, e.g., P3HT), ionic conducting electronic insulator 176 (e.g., an ion-gel), floating gate electrode 174, aqueous buffer 172 (e.g., 1× PBS), and the primary gate electrode 170. It will be observed that there is no noticeable loss of potential at the primary gate electrode 170 or floating gate electrode 174 interface with the aqueous electrolyte. $\Delta V_0$ and $\Delta V_{FG}$ represent the voltage drop at the ion-gel/P3HT interface (i.e., between ionic conducting electronic insulator 176 and semiconductor 178 at voltages 179A and 179B) that induces holes in the P3HT and, ultimately, the observed drain current.

In various examples described herein, such as in example device 20, the area of the interface of floating gate 30 and ionic conducting electronic insulator 32 can have dimensions of 1 mm×1 mm; the interface of floating gate 30 and aqueous buffer 38 can have dimensions 3 mm×3 mm; and primary gate electrode 22 can have dimensions 5 mm×5 mm. In some examples, these electrodes can be intentionally oversized to avoid undesirable effects from parasitic capacitance. Other example sizes of each electrode are also contemplated in other examples.

Figure 7A:
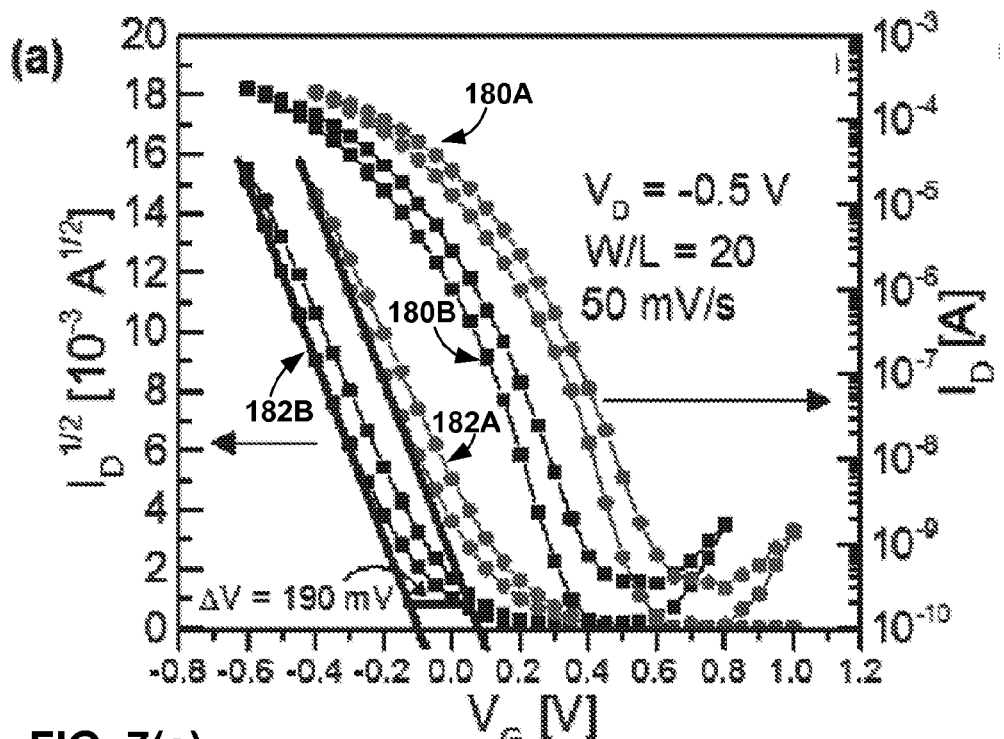
FIGS. 7A and 7B are graphs illustrating example effects of probe immobilization on the conductance of the EGT of FIGS. 1A-1D.
Figure 7B:
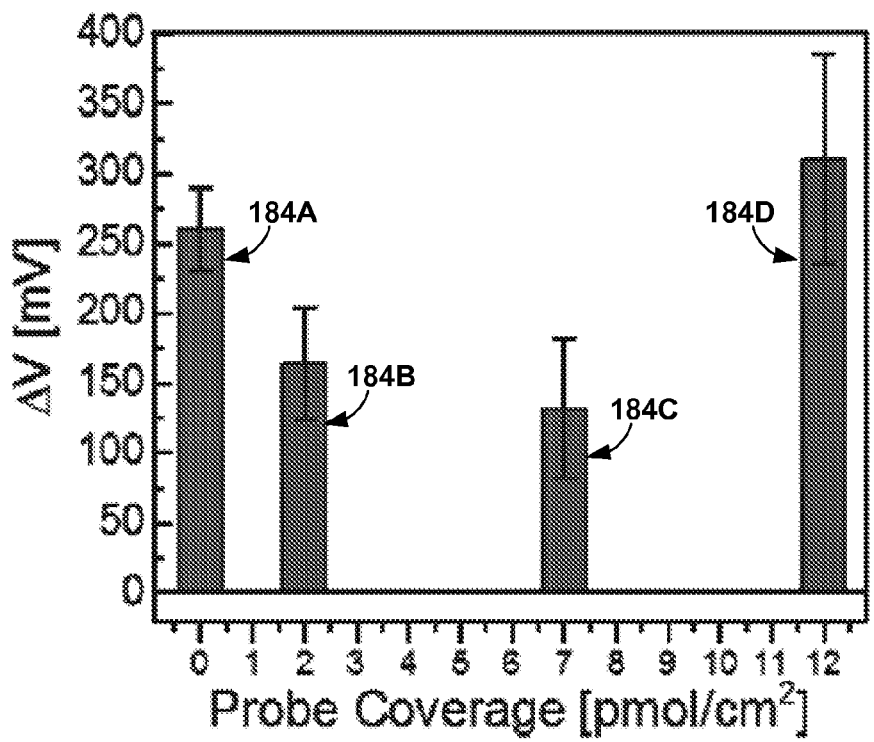

FIGS. 7A-7C illustrate the effect of probe immobilization in accordance with some examples. It will be noted upon examination of FIG. 7A-C that chemisorption at floating gate 30 results in charge separation in the form of interfacial dipoles which alter the effective gate voltage (e.g., $\Delta V_T$). FIG. 7A shows the positively shifted transfer curves for an example device that was tested before (curves 180A and 182A) and after (curves 180B and 182B) chemisorption of ssDNA at the interface of floating gate 30 and aqueous buffer 38 (see FIG. 1C). FIG. 7B summarizes the observed shifts in $V_T$ for different compositions of monolayers. The variability observed between each of bars 184A, 184B, 184C, and 184D at different probe coverages may be caused by variations in the number of chemical bonds, such as gold-sulfur bonds, present at the surface of second arm 40 for different functionalization techniques.

Figure 8:
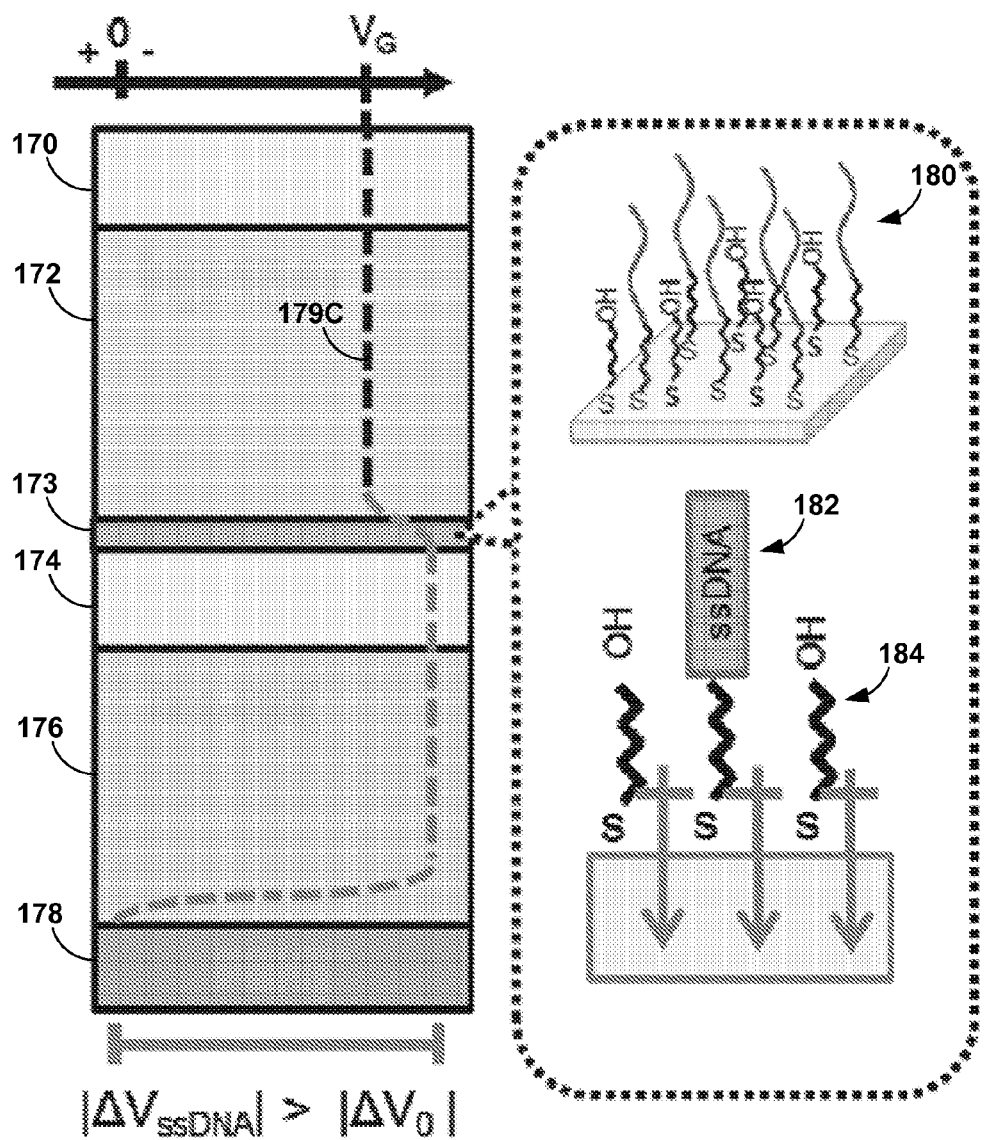
FIG. 8 is a conceptual illustration of the offset of a potential profile through the device of FIGS. 1A-1D.

FIG. 8 illustrates a simplified electrical potential profile through the device (e.g., device 20) for a negatively applied $V_G$, with particular attention to the offset at the interface between floating gate electrode 174 and aqueous buffer 172. This interface is represented by surface 173, which may include molecules 180 prior to the application of the target molecules. Molecules 180 may include probe molecules 182 configured to bind with other target chemical compositions and blocking molecules 184. Blocking molecules 184 may not be provided in all examples; however, such molecules may have significant utility where an analyte preparation may contain significant quantities of non-target molecules. Also as illustrated in FIG. 8, the origin of offset in voltage 179C over surface 173 may be related to the interfacial dipole formed between gold and sulfur atoms, or between other atoms if different materials are used for floating gate electrode 174. This bond is formed by sulfur donating electron density to the underlying gold substrate of the floating gate electrode resulting in the dipole orientation presented with arrows. As a result of this voltage offset, the P3HT semiconductor 178 is more conducive at a given $V_G$, since the interfacial drop is increased ($\Delta V_{ssDNA} > \Delta V_0$) as shown as the shift in voltage 179C at surface 173.

Figure 9A:
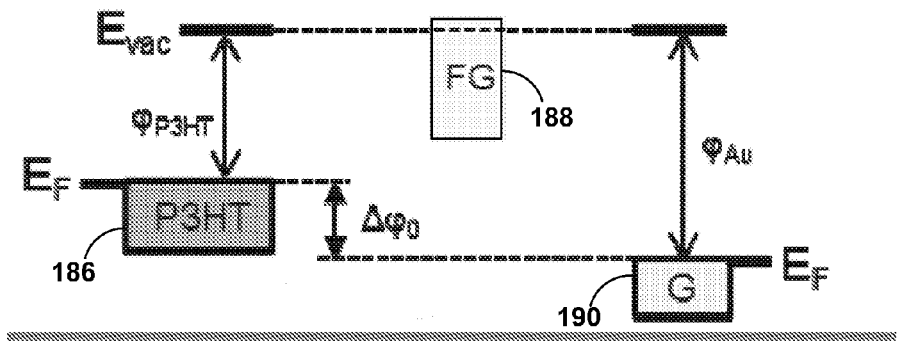
FIGS. 9A-9C are conceptual illustrations of example energy diagrams of the bond dipoles at the interface of the floating gate of an example EGT and an aqueous electrolyte.

FIG. 9A shows the vacuum level alignment between primary gate 190 (G) and P3HT semiconductor 186 before chemisorption of ssDNA to the interface of floating gate 188 and before electrical connection (equilibrium). The difference between the vacuum level and Fermi level is referred to as the work function ($\varphi$), and is different for P3HT semiconductor 186 and gold substrate ($\Delta \varphi_0$).

Figure 9B:
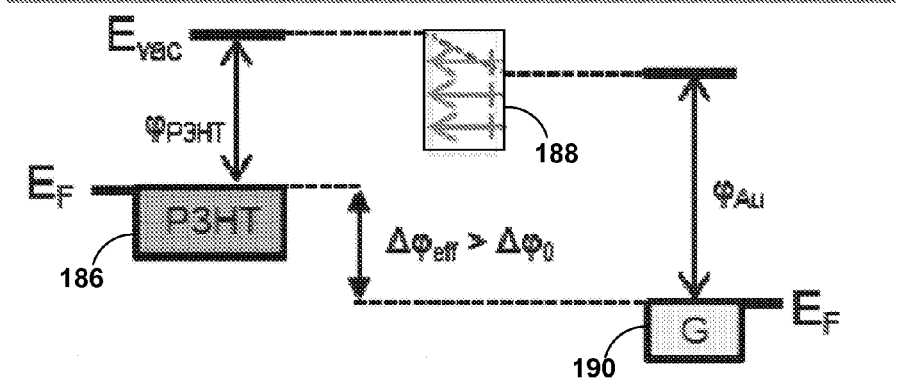

In FIG. 9B, chemisorption of ssDNA and MCH at the interface of a floating gate electrode and an aqueous electrolyte is represented as a dipole 188 oriented toward the Au atoms of the Au—S bond. The immobilization of dipole 188 offsets a vacuum level, which raises the effective work function of primary gate electrode 190, thereby causing the effective work function difference between P3HT semiconductor 186 and primary gate electrode 190 to increase ($\Delta \varphi_{eff} > \Delta \varphi_0$).

Figure 9C:
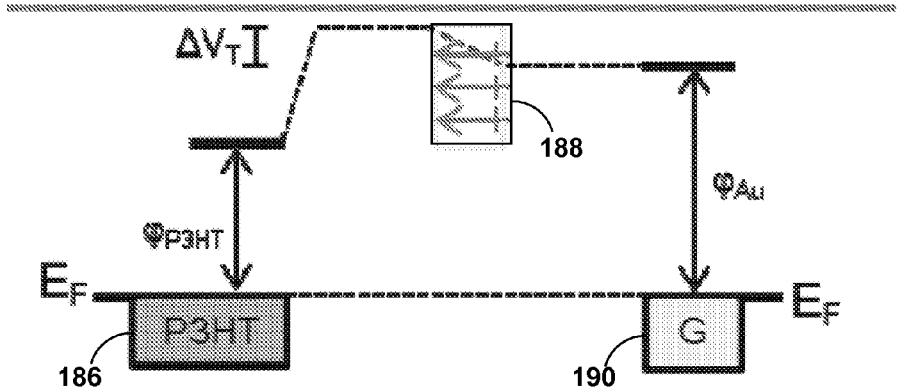

During testing, the Fermi levels align. FIG. 9C demonstrates the offsetting of a vacuum level in response to the immobilized dipole, resulting in a shift of the potential at the interface of P3HT semiconductor 186 and an ion-gel. This shift in potential is observed as a change in threshold voltage ($\Delta V_T$) during device testing and a resulting alteration of the potential profile between semiconductor 186 and primary gate electrode 190.

FIG. 10 is a conceptual illustration of the effect of DNA hybridization on a potential profile of example device 20. FIG. 10 illustrates simplified electrical potential profiles 179D and 179E through the device (e.g., device 20) for a negatively applied $V_G$, with particular attention to the offset at the interface between floating gate electrode 174 and aqueous buffer 172 at surface 173 of floating gate electrode 174. Before the target molecules are added, surface 173 may include probe molecules 194 (e.g., single-stranded DNA). Upon the addition of a target molecule having complementarity with probe molecules 194, probe molecules 194 complex with target molecules, resulting in hybridized molecules 196. Hybridized molecules 196 may be bonded to the surface 173 in addition to blocking molecules, as generally depicted by bonded molecules 192. The offset in voltage for potential profile 179D over surface 173 is larger for probe molecules 194 than the potential profile 179E of hybridized molecules 196, thereby indicating that a target molecule is present. A result of this voltage offset, ($\Delta V_{ssDNA} > \Delta V_{dsDNA}$) is shown in FIG. 10 as the shift in profiles between 179D and 179E.

Figure 11A:
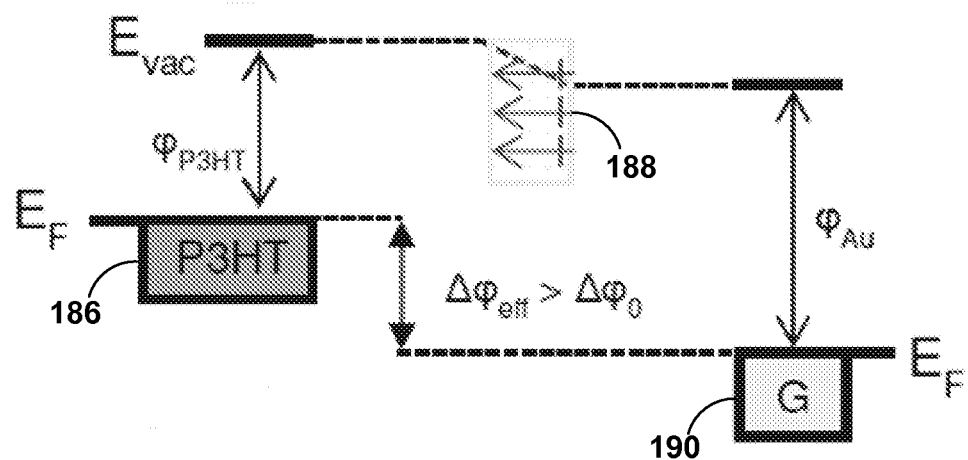
FIGS. 11A and 11B are conceptual illustrations of energy diagrams of the bond dipoles at the interface of the EGT of FIGS. 1A-1D and the aqueous electrolyte of FIGS. 9A-9C after ssDNA adsorption and after dsDNA formation.
Figure 11B:
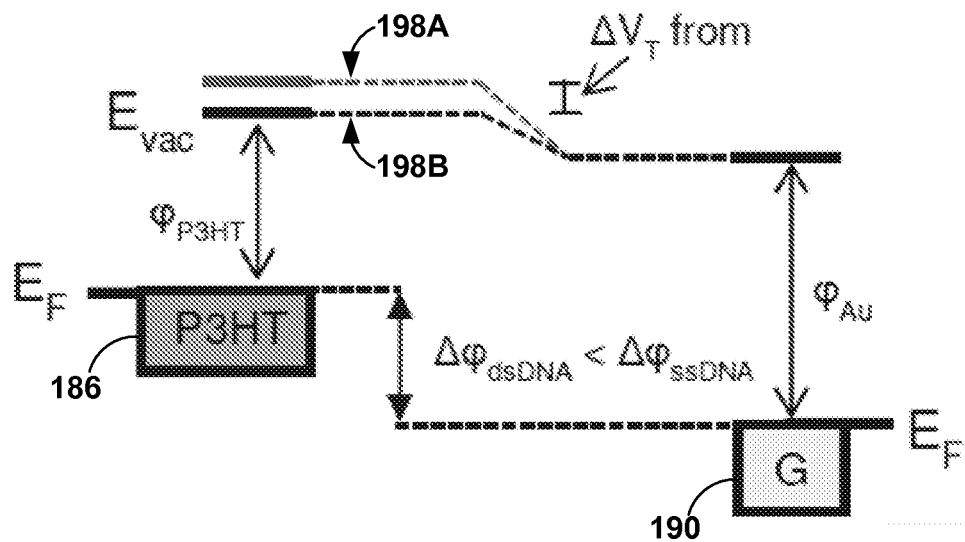

FIGS. 11A-11B are conceptual illustrations of energy diagrams of the bond dipoles at the interface of example device 20 and aqueous electrolyte 38 of FIGS. 1A-1D following chemisorption of ssDNA and subsequent dsDNA formation. In FIG. 11A, interface 188 of a floating gate electrode and an aqueous electrolyte is represented as a dipole in the orientation of the Au—S bond which offsets the vacuum level when the probe molecules are present. This raises the effective work function of primary gate electrode 190 causing the effective work function difference between P3HT semiconductor 186 and primary gate electrode 190 to increase ($\Delta\varphi_{eff} > \Delta\varphi_0$). FIG. 11B shows the energy change between ssDNA at energy level 198A and dsDNA at energy level 198B. In turn, alterations of the interfacial capacitance (e.g. from DNA hybridization) offset $V_T$.

FIG. 12 is a graph illustrating the effects of ssDNA adsorption and dsDNA formation on the conductance of floating gate electrode 30 of example device 20. Curve 200 represents the I-V characteristic of floating gate electrode 30 prior to the addition of ssDNA, as shown in FIG. 1B, and curve 202 shows the current measured after the addition of ssDNA. Curve 204 shows the current measured after hybridization with complementary DNA to result in dsDNA. For this sample, the initial $V_T$ was −0.09 V, the ssDNA curve 202 shifted +0.30 V, and the dsDNA curve 204 shifted −0.15 V from ssDNA curve.

Figure 13:
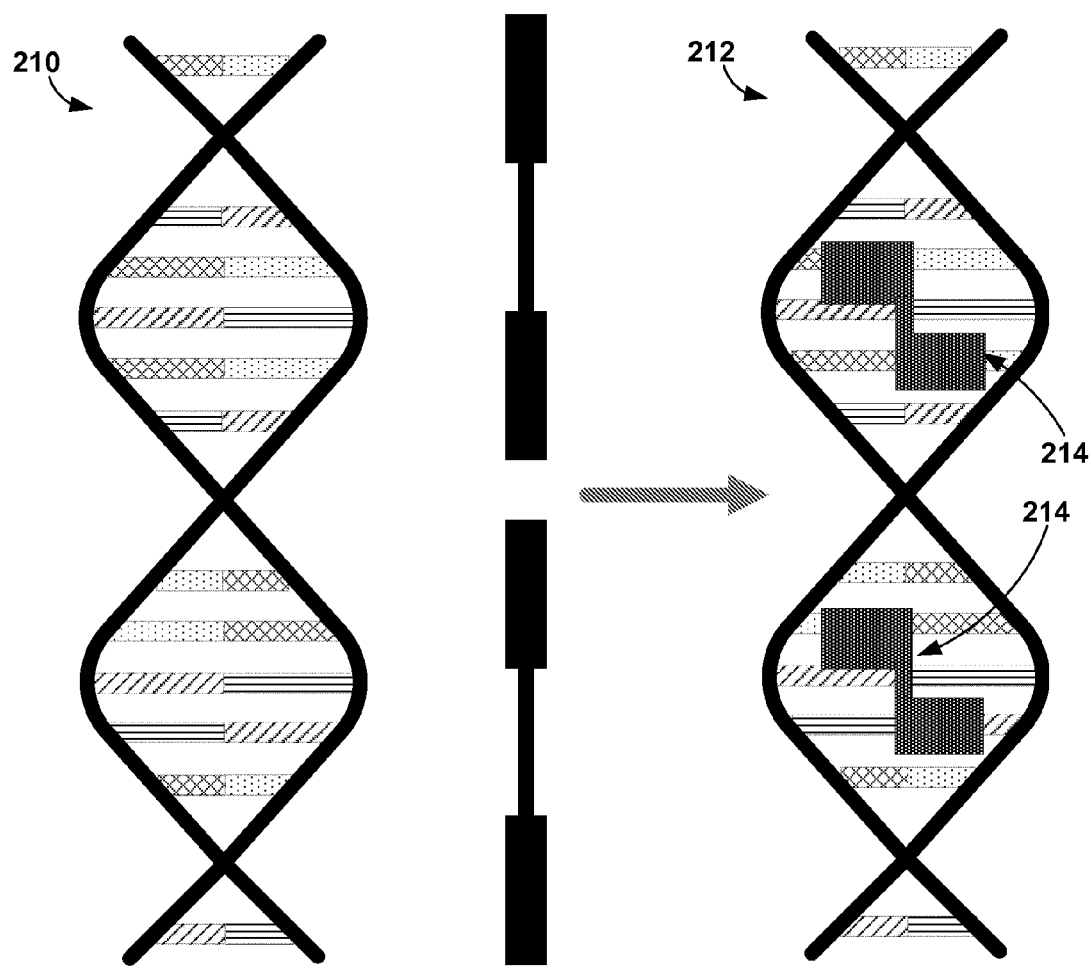
FIG. 13 is a conceptual illustration of the use of a dye employed in the generation of fluorescent images of gold substrates.

FIG. 13 is a conceptual illustration of the use of dye 214 employed in the generation of fluorescent images of gold substrates, which can be used to indicate the presence of absence of probe molecules on a substrate of a floating gate electrode, for example. Samples of DNA 210 can be immersed in dye 214, which, in some examples, may consist of YOYO-1 (a bisintercalating dye that intercalates among bases in a nucleic acid and exhibits a ~1000-fold increase in fluorescence when in the presence of dsDNA), thereby resulting in DNA/dye complex 212.

Figure 14:
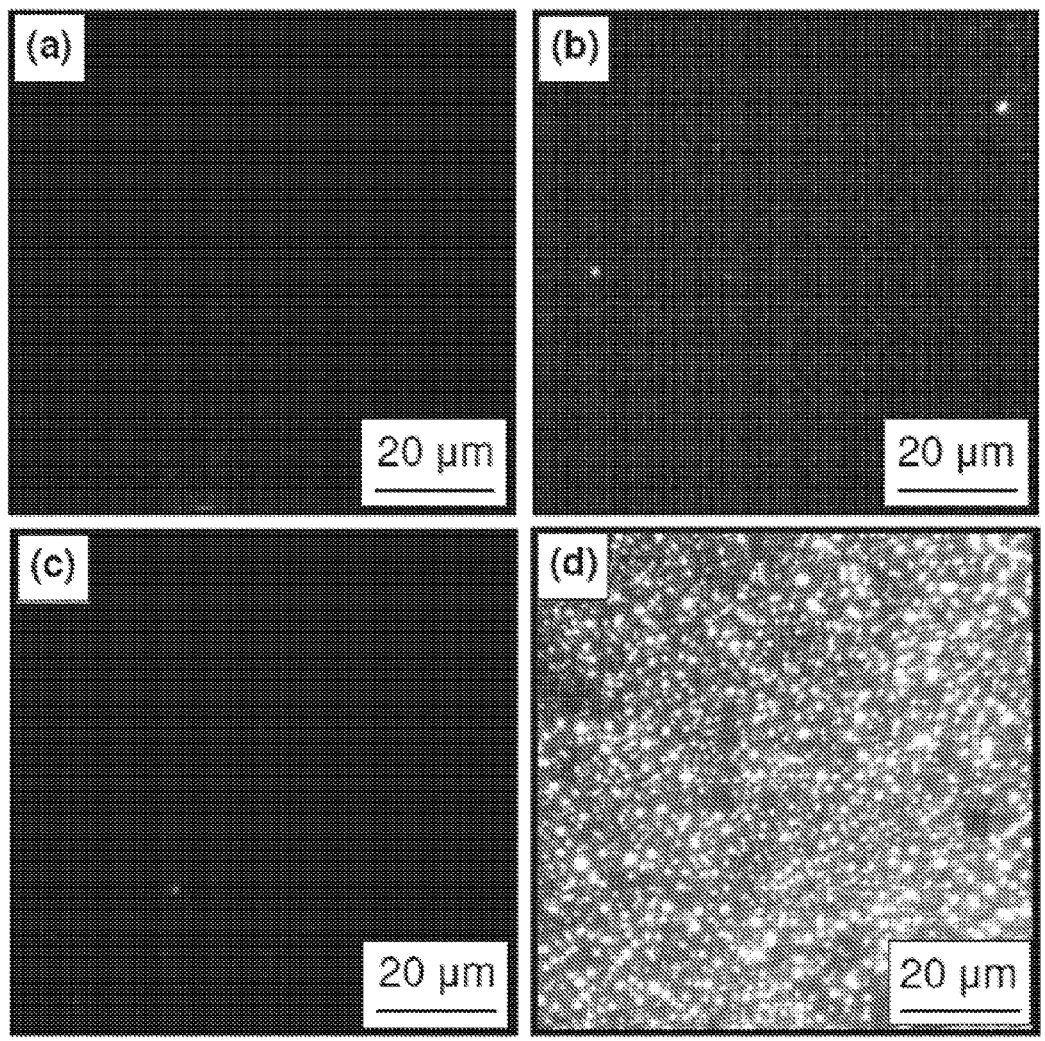
FIG. 14 includes different illustrations of the example fluorescence observed following the addition of the dye of FIG. 13 to a gold substrate in the presence or absence of probe molecules, blocking molecules, and target molecules.

FIG. 14 includes different illustrations of the example fluorescence observed following the addition of dye 214 of FIG. 13 to a gold substrate in the presence or absence of probe molecules, blocking molecules, and target molecules. Image (a) is of a bare gold substrate. Image (b) is a sample functionalized with a medium density of probes and MCH. Image (c) illustrates the exposure of probes to random DNA. Image (d) illustrates the drastic increase in fluorescence observed when probes are exposed to complementary DNA. Image (d) illustrates a confirmation that the surface of floating gate electrode 30 is becoming sufficiently hybridized.

Figure 15A:
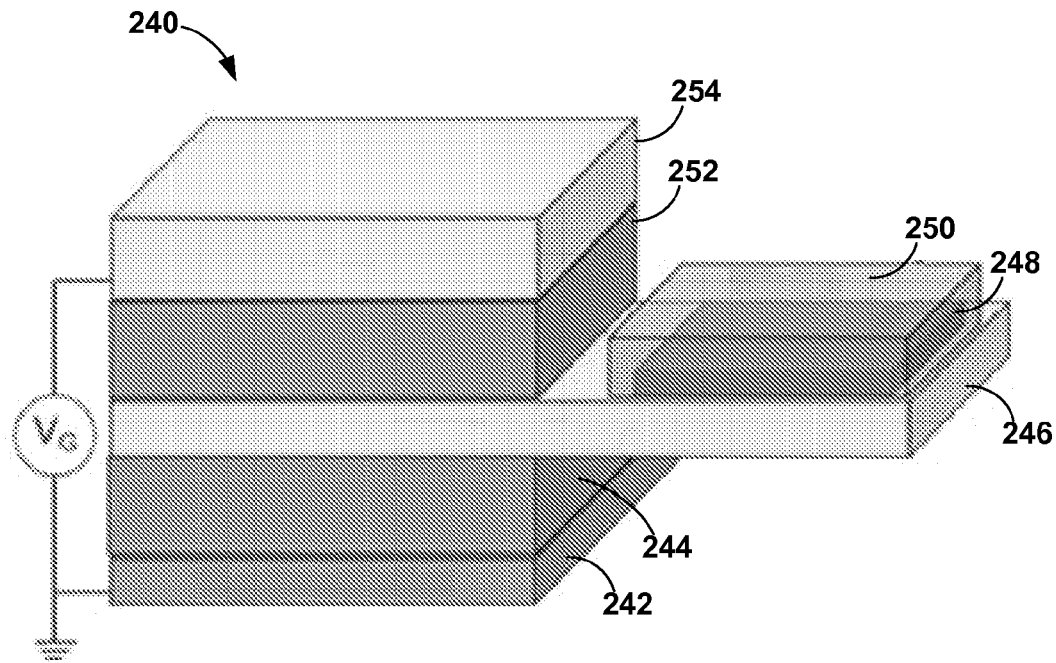
FIGS. 15A and 15B are conceptual diagrams of example analyte locations for a device used to detect the presence of a target molecule.
Figure 15B:
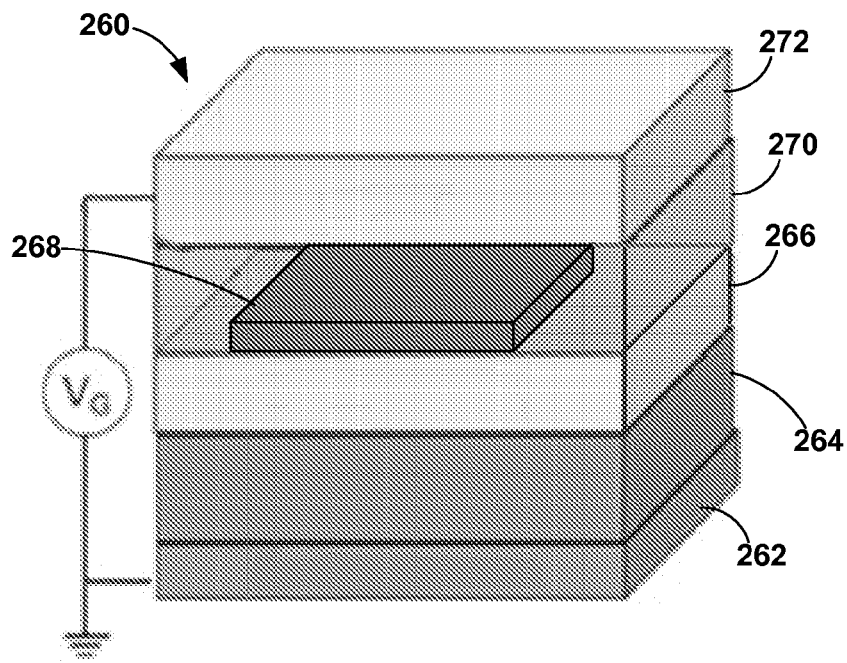

FIGS. 15A-15B are conceptual diagrams of example analyte locations for devices used to detect the presence of a target molecule. FIG. 15A illustrates device 240 having technology with floating-gate biosensors. Device 240 has a semiconductor layer 242 coupled to a solid dielectric layer 244. Solid dielectric layer 244 is coupled to floating gate electrode 246, and floating gate electrode 246 is coupled to solid dielectric layer 252 at one portion and analyte 248 and water 250 at a second portion. Solid dielectric layer 252 is then coupled to primary gate electrode 254. It will be appreciated that the biosensor of device 240 interacts with DNA at a floating-gate/water interface which is not a core element of the device.

In contrast to device 240 of FIG. 15A, as will be appreciated by examination of FIG. 15B, analytes 268 of device 260 are located in the floating gate transistor (e.g., between primary gate electrode 272 and floating gate electrode 266) in some examples. In particular, analytes 268 are located at the interface of floating gate electrode 266 and aqueous electrolyte 270. In this manner, device 260 may be similar to device 20 described herein. Specifically, device 260 includes a semiconductor layer 262 coupled to ion-gel layer 264. Ion-gel layer 264 is coupled to floating gate electrode 266, and floating gate electrode 266 is coupled to primary gate electrode 272 via analytes 268 and an aqueous dielectric layer 270.

As discussed herein, floating-gate organic transistors with electrolyte dielectrics can have applications in emerging biosensing technologies. In contrast to oxide dielectrics, the mobile ions in the electrolyte of a floating gate transistor may require different geometric design considerations. Introduction of a floating gate electrode may require modification of the circuit to account for charge storage in the floating gate that enhances the device sensitivity to changes in floating-gate capacitance. In some examples, a floating gate can be selectively functionalized with self-assembled monolayers (SAM) to observe how changing the work function of a floating gate may altered the effective gate voltage. In some examples, the direction of the voltage change may be dependent on the orientation of the SAM while remaining independent of the end group chemistry of the SAM, due to charge screening by electrolyte ions. Functionalization is discussed with regard to FIGS. 16-18B, for example.

Figure 16:
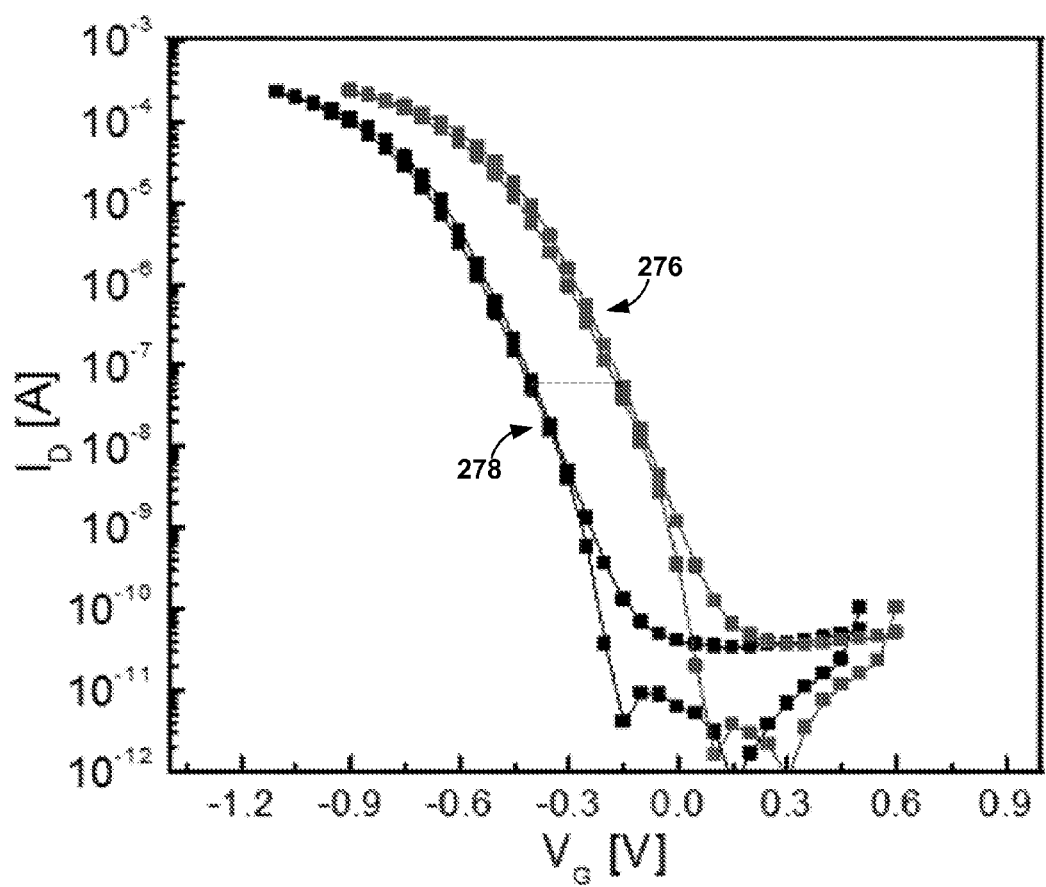
FIG. 16 is a graph illustrating example data representative of the change in threshold voltage following surface functionalization of the surface of the floating gate.

FIG. 16 is a graph illustrating example data representative of the change in threshold voltage following surface functionalization (e.g., with a SAM) of the surface of floating gate electrode 30 of example device 20. Curve 278 indicates the threshold voltage of floating gate electrode 30 prior to functionalization, while curve 276 indicates the threshold voltage following functionalization with a SAM.

To fabricate devices functionalized with SAMs, in some examples, P3HT can be printed onto a wafer with patterned electrodes to a thickness of 50 nm, and then heated to 120° C. for 1 hour in a nitrogen environment to anneal the polymer film. Microfluidic channels can be aligned by hand, reversibly bonded to the substrate by plasma treating only the poly(dimethylsiloxame) (PDMS) molds into which the microfluidic channels were imprinted, and then held at room temperature. This method of fabrication may be used instead of the standard process of plasma treating both the PDMS mold and substrate, and then heating at 75° C. for 2 hours. To prepare the SAM molecules (MCH or NFH) for assembly at a floating gate, SAM molecules may be diluted to 1 mM in distilled water (for MCH) and a 1:1 by volume mixture of ethanol and water (for NFH). The solution can then be selectively flowed over one side of a floating gate electrode at 1 uL/min, allowed to absorb at room temperature for 2 hours, followed by rinsing with solvent. Finally, the microfluidic channels can be removed so that an ionic conducting electronic insulator may be printed over the electrodes.

The metal/organic interface can be modified by chemisorbing a self-assembled monolayer (SAM) of alkyl-thiol derivatives. This process changes the interfacial electronic energy, which is interpreted as a change in the work function of the underlying metal. Immobilizing alky-thiols onto the electrodes of an EGT can alter the injection barrier of carriers into the semiconductor when bound to the source/drain electrodes and also to tune the threshold voltage of an EGT when bound to the dielectric layer.

In some examples, the SAM used to alter the work function of a floating gate may be formed of molecules such as 1-mercaptohexanol (MCH) (HS—$(CH_2)_5$—CH3) or non-afluorohexane thiol (NFH) (HS—$(CH_2)_2$—$(CF_2)_3$—$CF_3$). MCH is commonly used to passivate sensing surfaces and, like many alkyl-thiol derivates, is expected to lower the work function of the underlying metal while the fluorinated NFH will raise it. The molecules were selectively deposited onto the semiconductor side of the floating gate electrode or the primary gate side of the floating gate electrode by flowing them through reversibly bonded microfluidic channels, rinsing/drying, removing the microfluidic channels, then printing an ionic conducting electronic insulator over the functionalized electrode.

Via experimentation, there is a clear dependence of the direction in which an observed transfer curve may shift in response to a SAM on the location of the SAM relative to the floating gate, but not on the chemistry of the SAM. FIG. 16 shows that NFH on the primary gate electrode side of the floating gate electrode shifts the threshold voltage positively, from curve 278 with no functionalization to curve 276 with functionalization. NFH on the semiconductor side shifts the curve negatively. This result is similar for MCH. The work function of gold electrodes functionalized with MCH and NFH can be approximately: $\Delta\varphi = -230 \pm 10$ meV for MCH and $\Delta\varphi = +340 \pm 5$ meV for NFH when measured with Scanning Kelvin Probe Microscopy (SKPM) in an inert environment (Argon).

When the molecule is chemisorbed on the primary gate side of the floating gate, the electron energy of primary gate with a SAM is $E_G^2 = (\varphi_{P3HT} - \varphi_{Au}) + (\varphi_{SAM} - \varphi_{Au})$ and without a SAM is still $E_G^0 = \varphi_{P3HT} - \varphi_{Au}$. The polarity of the SAM is opposite from when it was on the semiconductor side and $\Delta V_T = \varphi_{Au} - \varphi_{SAM}$. As a result, the $V_T$ shift in FIG. 16 has the opposite direction as the $V_T$ shift for functionalized floating gate on the semiconductor side because lowered work functions result in positive $V_T$ shifts due to the different orientation of the SAM with respect to the P3HT film.

Figure 17A:
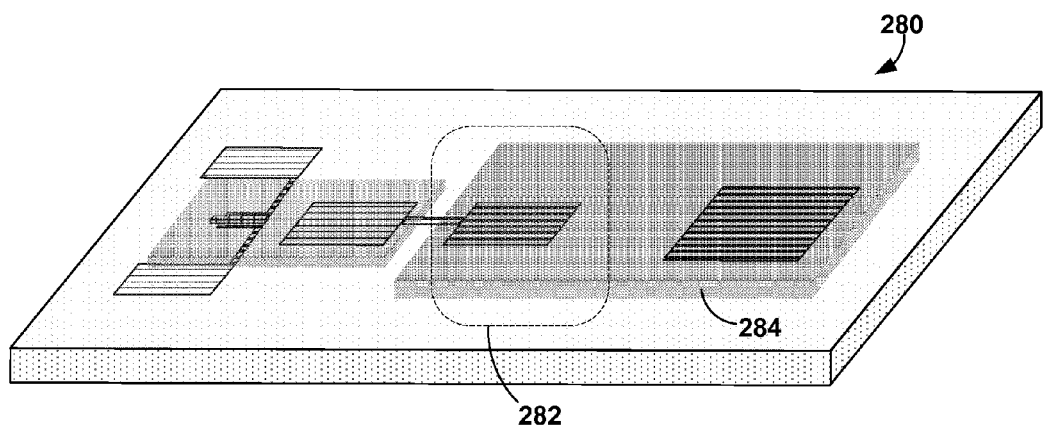
FIGS. 17A and 17B are conceptual diagrams of the location and chemical composition of molecules that may be used to functionalize the surface of a floating gate electrode.
Figure 17B:
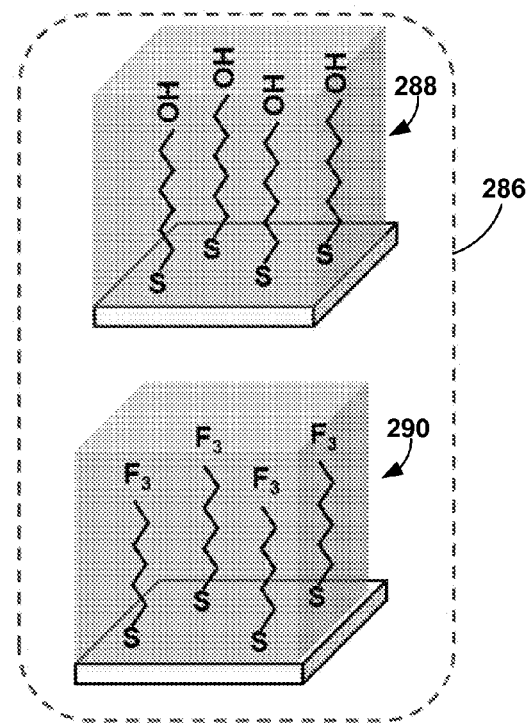

FIGS. 17A and 17B are conceptual diagrams of the location and chemical composition of molecules that may be used to functionalize the surface of a floating gate electrode in device 280 (e.g., device 280 may be similar to device 20). As shown in FIG. 17A, the portion of the floating gate electrode outlined in area 282 coupled to the primary gate electrode via the aqueous buffer 284. Surfaces 286 of FIG. 17B show that probe molecules 288 can be coupled to the surface of the electrode. Functionalization molecules 290 can alternatively be deposited to the surface of the electrode to achieve shifts in potential.

Figure 18A:
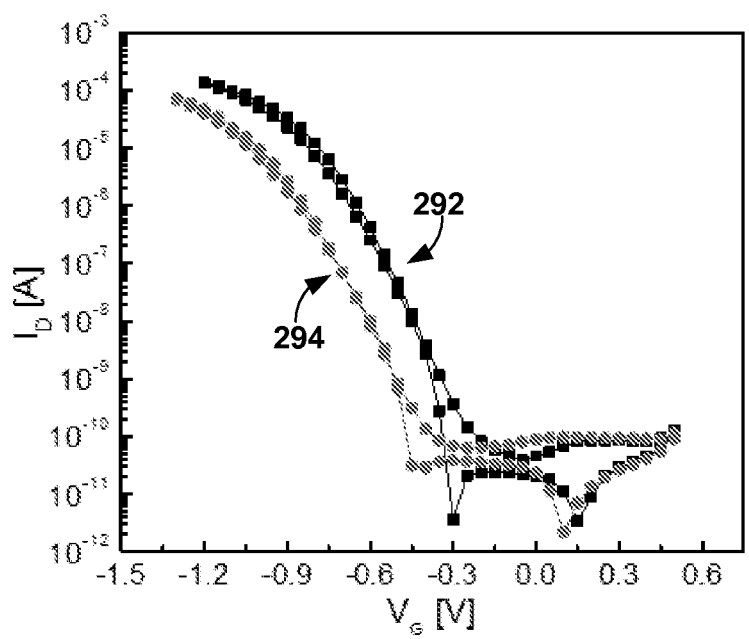
FIGS. 18A and 18B are graphs illustrating the relative capacitance sensitivities of conventional electrodes and floating gate electrodes.
Figure 18B:
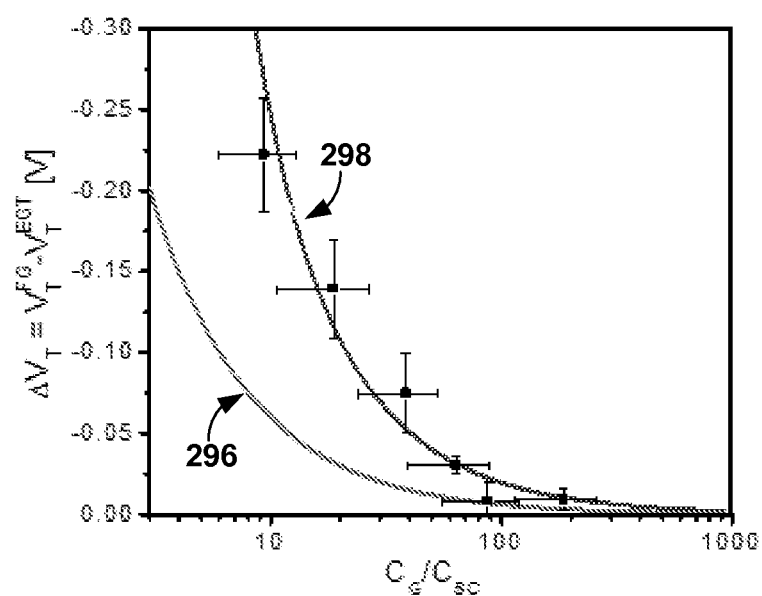

FIGS. 18A and 18B are graphs illustrating the relative capacitance sensitivities of conventional electrodes and floating gate electrodes. As shown in FG. 18A, curve 292 is an $I_D$-$V_G$ curve for larger floating gate electrode area than a floating gate area that produces the $I_D$-$V_G$ curve 294. In other words, smaller areas of a floating gate electrode may result in more negative $V_T$ shifts, in some examples. As shown in FIG. 18B, smaller areas for a floating gate electrode require higher (more negative) voltages to reach the same $I_D$ as a larger electrode. Curve 296 and curve 298 depict a significant increase in capacitance sensitivity generated at different threshold voltages, based on different calculations.

In some examples, a floating gate transistor utilizing electrolyte dielectrics has fundamental differences from its inorganic counterpart. Geometric considerations can be considered in order to avoid undesirable effects such as parasitic capacitance and hysteresis in an EGT. When operating with a floating gate electrode, the device response is even more sensitive to interfacial capacitance due to the ability of the floating electrode to store charge. With simple approximations, a linear circuit of double-layer capacitors can accurately describe these characteristics.

The flexible processing of organic electronics allows a device, e.g., a floating gate EGT such as device 20, to be readily functionalized from solution through microfluidics. The formation of a SAM at floating gate electrode 30 results in $V_T$ shifts having a direction dependent on the orientation of the SAM with respect to the P3HT film, but largely independent of the functional group chemistry of the SAM. The former effect provides a method to tune the threshold voltage of a low-voltage EGT, while the latter effect illustrates the importance of electrolyte chemistry on the electronic surface potential (work function) of the underlying electrode. A sensor (e.g., device 20) utilizing a floating gate EGT can be designed by interacting molecules on the primary gate side of the floating gate. A SAM designed to selectively capture the analyte is first formed which causes a positive $V_T$ shift due to a lowered work function of the floating gate. The subsequent binding of analyte molecules to this SAM result in negative $V_T$ shifts attributed to changes in interfacial capacitance, rather than changes in work function.

Figure 19:
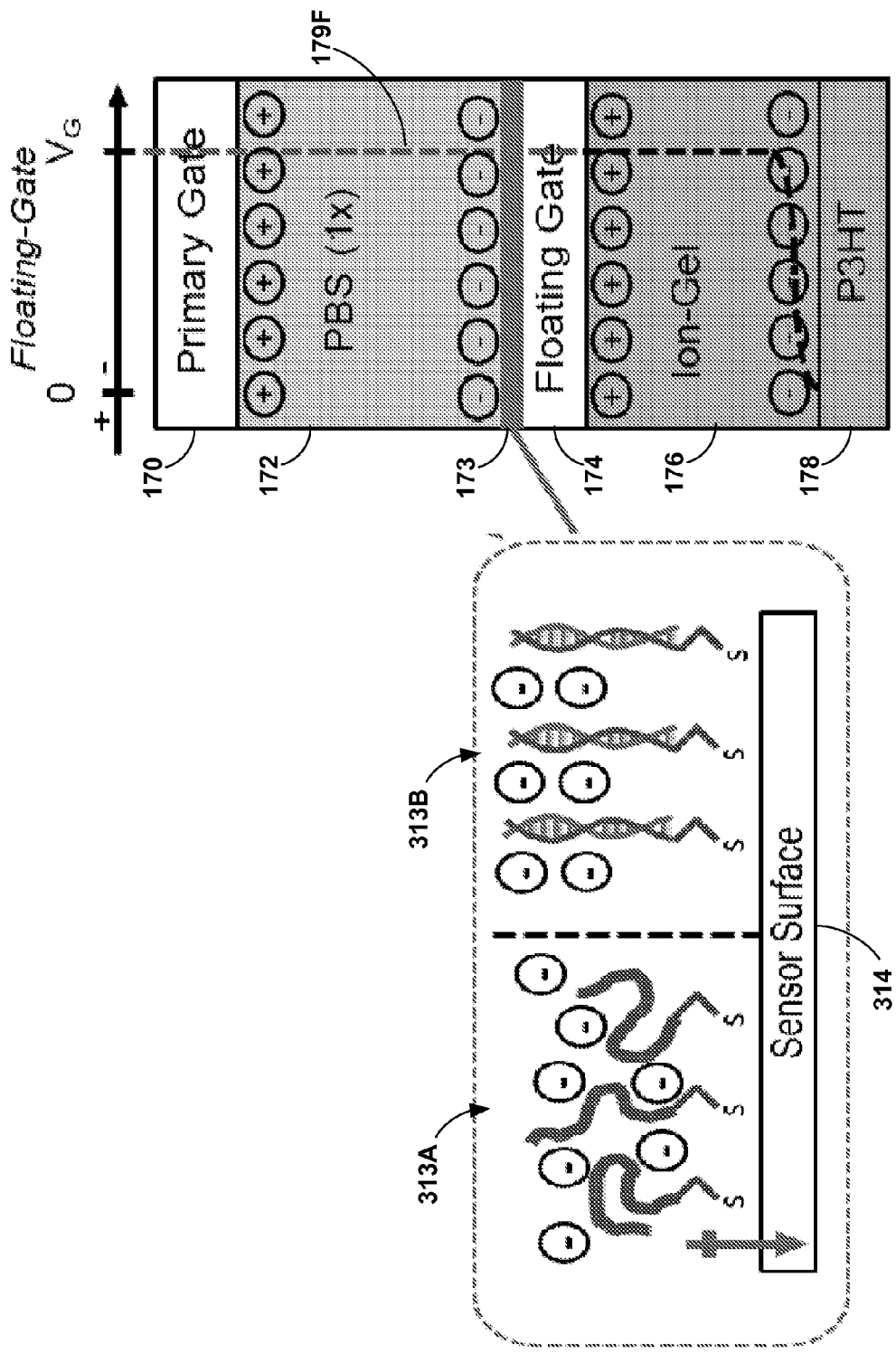
FIG. 19 is a conceptual illustration of example offsetting of potential profiles through the floating gate electrode of the EGT of FIGS. 1A-1D in response to ssDNA adsorption and dsDNA formation.

FIG. 19 is a conceptual illustration of example offsetting of potential profiles through the floating gate electrode of an EGT in response to ssDNA adsorption and dsDNA formation. As shown in the example of FIG. 19, an example device may include semiconductor 178 (e.g., P3HT), ionic conducting electronic insulator 176 (e.g., an ion-gel), floating gate electrode 174, surface 173 between floating gate 174 and aqueous buffer 172, aqueous buffer 172 (e.g., 1× PBS), and primary gate electrode 170. Voltages 179F are shown throughout the stack of layers in the device. On the sensor surface (e.g., surface 173 of floating gate 174), ssDNA probe molecules 313A are unorganized. Upon hybridization, dsDNA molecules 313B shift the potential in a more negative direction.

Figure 20:
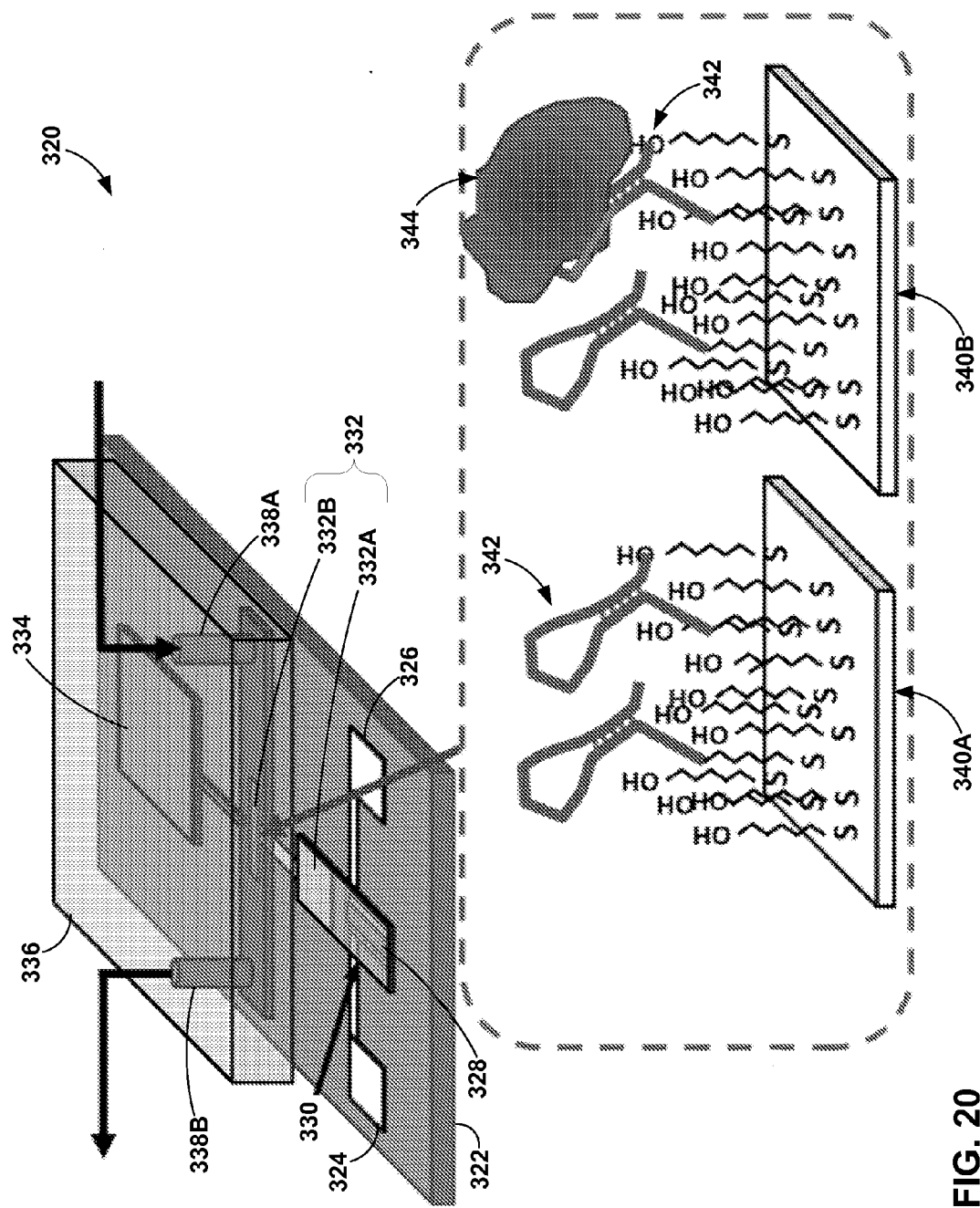
FIG. 20 is a conceptual illustration of an example device configured to detect a target protein molecule.

FIG. 20 is a conceptual illustration of an example device 320 configured to detect a target protein molecule 344. As shown in FIG. 20, device 320 may include a floating gate transistor similar to device 20. Device 320 may include a substrate 322 having source electrode 324, drain electrode 326, semiconductor 328 deposited thereto. In addition, floating gate electrode 332 (shown in FIG. 20 as having first portion 332A and second portion 332B) may be coupled to semiconductor 328 via ion-gel 330 (via first portion 332A) and second portion 332B of floating gate electrode 332 may be coupled to primary gate electrode 334 via aqueous buffer 336. To permit the introduction of a sample that may contain the target molecules to second portion 332B of the floating gate electrode 332 in contact with the aqueous buffer 336, microfluidic channels may be provided having inlet 338A and outlet 338B. Initially, probe molecules 342 may be bound to the interface of the second portion 332B of floating gate electrode 332, where probe molecules 342 may include a thiol group in some examples. If the sample provided via inlet 338A includes the target molecule for the probe molecules 342, protein molecule 344 may bind to a probe molecule 342 and produce observable shifts in voltage (similar to DNA hybridization described herein).

Figure 21A:
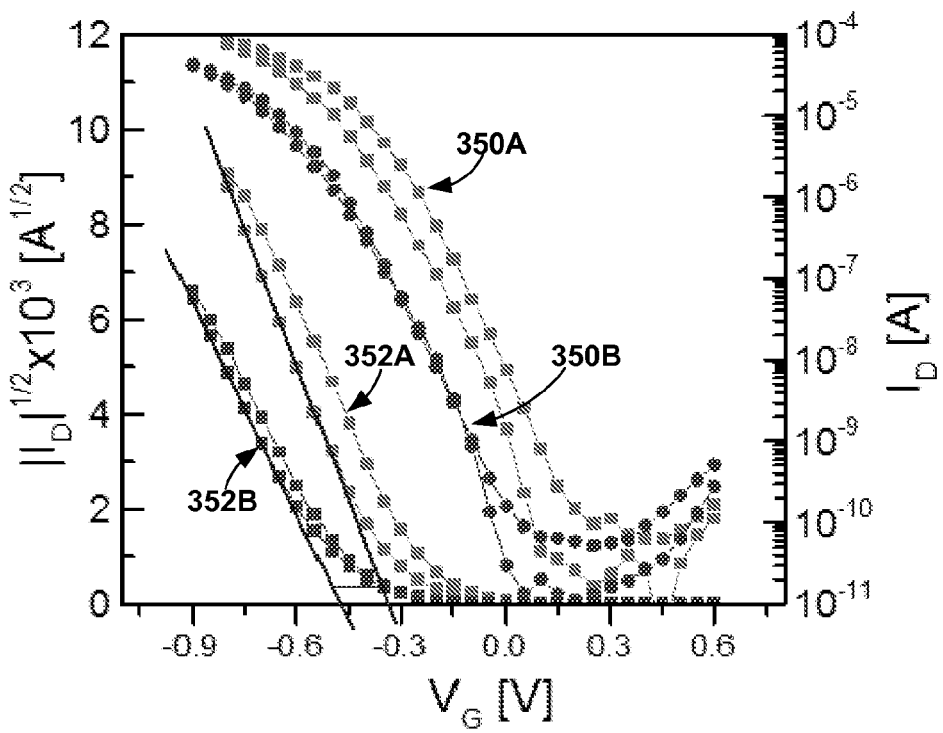
FIGS. 21A-21B are graphs illustrating example offsetting of potential profile through the example device in response to the adsorption of affinity reagents, target proteins, and control proteins to the surface of the floating gate electrode of the EGT of FIGS. 1A-1D.
Figure 21B:
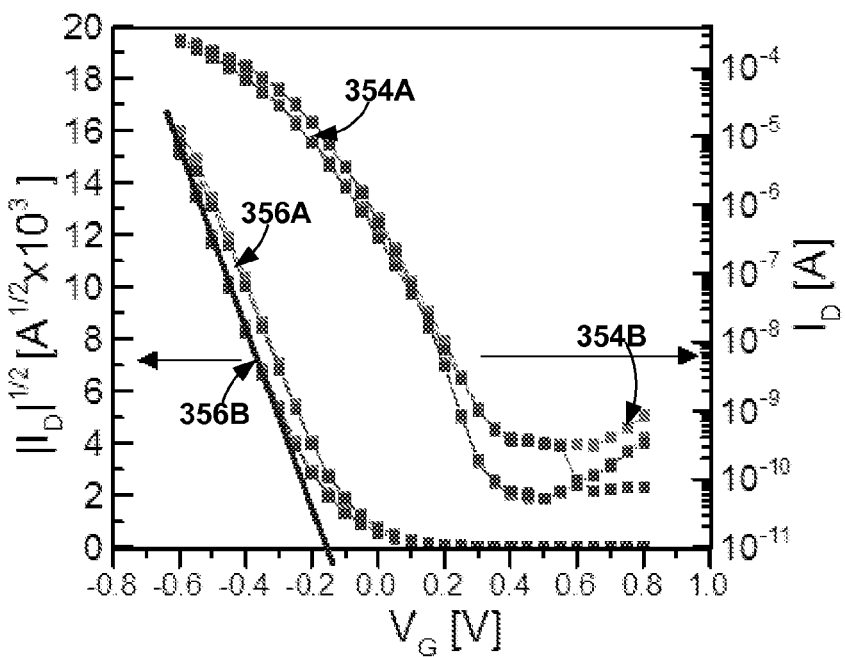

FIGS. 21A and 21B are graphs illustrating example offsetting of potential profiles through an example device in response to the adsorption of affinity reagents, target proteins, and control proteins to the surface of the floating gate electrode of an EGT. In the example of 21A, the difference in detected current between a probe molecule and a detected target molecule is illustrated. Curves 350A and 352A depict curves resulting from the use of an aptamer as a probe molecule to detect, in this example, the protein ricin. Curves 350B and 352B show that when ricin is detected, for example, the current shifts more negative. FIG. 21B shows that the curves for an aptamer 354B and 356B when not bound to the target protein are very similar to a present control protein, Bovine Serum Albumin (BSA). This indicates that the aptamers are selective for only the target protein.

Figure 22:
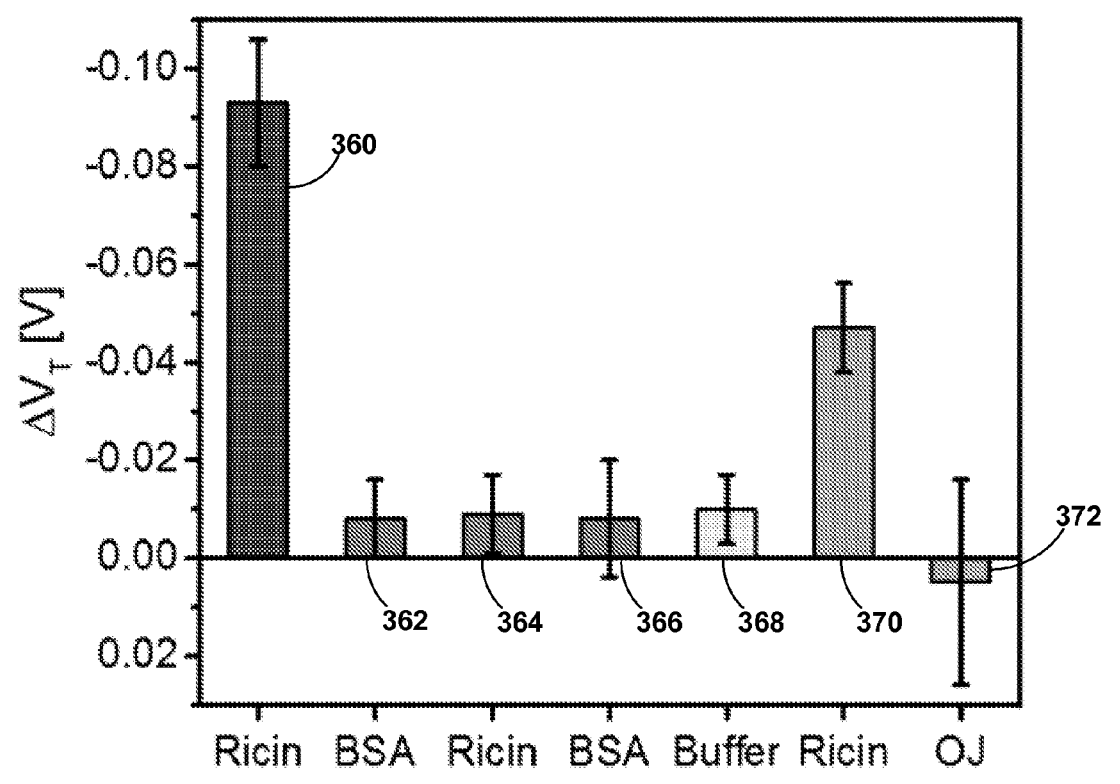
Figure 23:
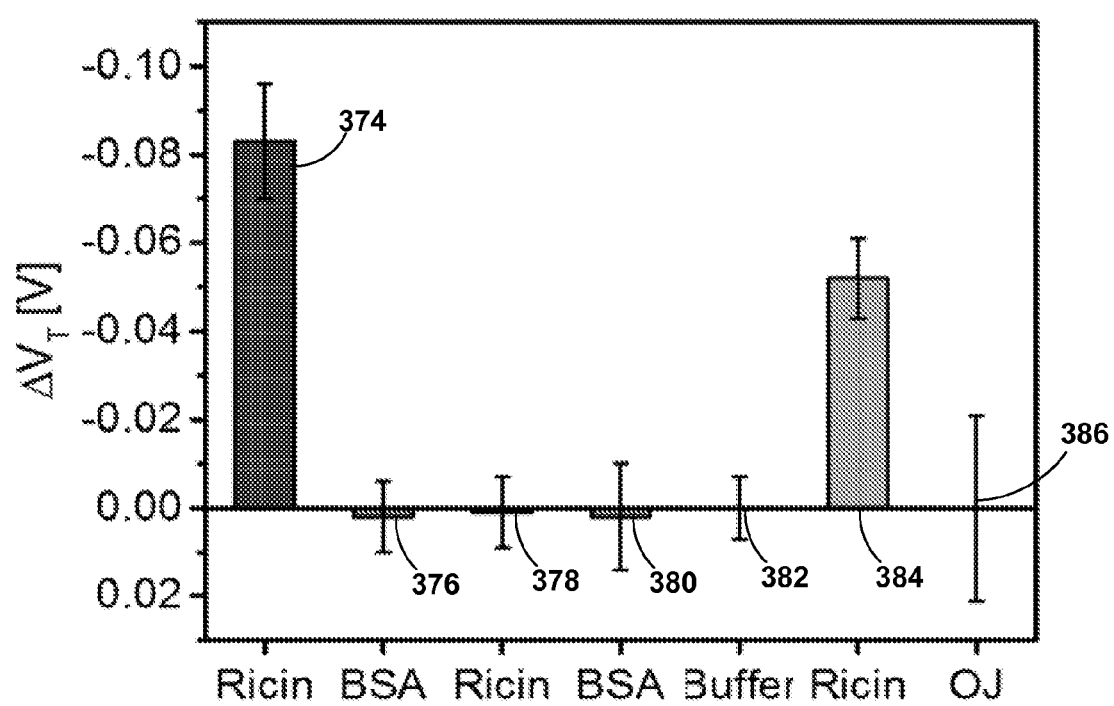

FIGS. 22 and 23 are graphs illustrating example experimental results of voltages measured in response to various target- and non-target compounds. As shown in the graph of FIG. 22, bar 360 shows the detection of ricin bound to its aptamer which indicates a positive result. Bars 362, 364, and 366 are combinations of the proteins BSA, ricin, and aptamers which are not selective to the desired targets. Bar 370 indicates the signal for orange juice and ricin, and bar 372 indicates the signal for only orange juice. As shown in FIG. 23, the graph shows the resulting signal when noise from bar 368 of FIG. 22 (when only PBS buffer is added with no protein present) is subtracted from the signals to provide a more robust detection signal. Bar 374 represents the aptamer and ricin signal, bar 384 represents the orange juice signal, and bars 376, 378, 380, 382, and 386 show the non-target substances.

Figure 24:
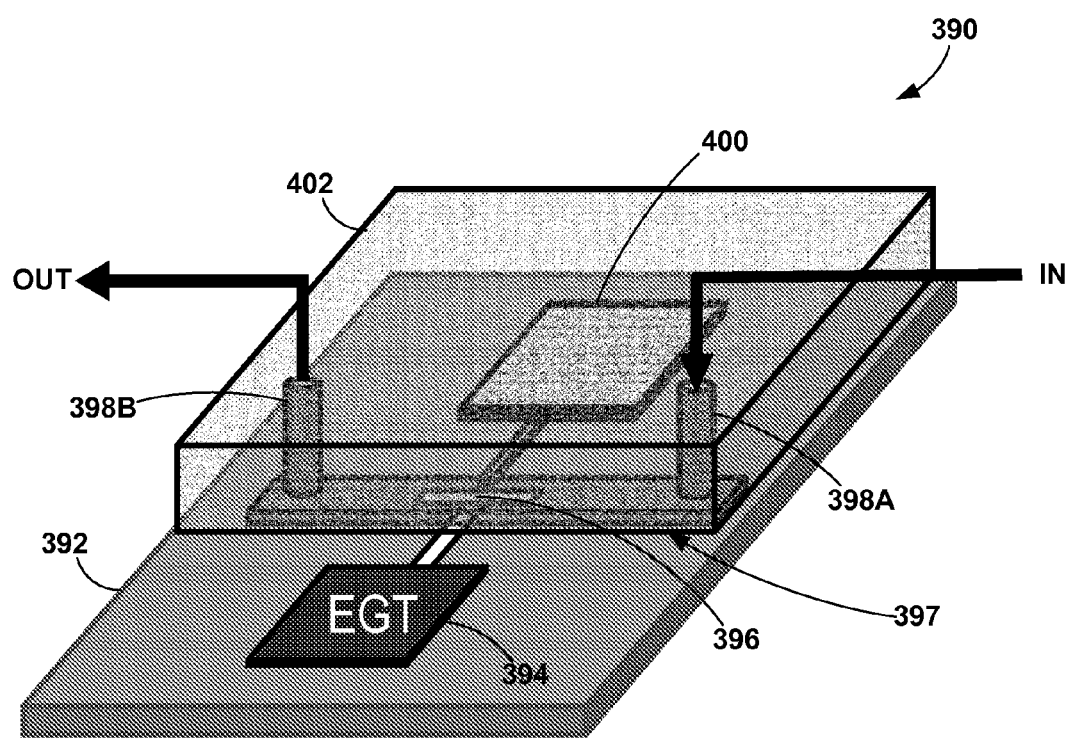
FIG. 24 is a conceptual illustration of a system that decouples sample handling and target protein detection.

FIG. 24 is a conceptual illustration of an example system 390 that includes a floating gate transistor. The separated input and output locations of system 390 may serve to decouple sample handling and target protein detection, which may serve to optimize the design of system 390 in terms of simplicity and improved performance System 390 includes a substrate 392 having an electrolyte gated transistor 394 coupled to a floating gate electrode 396. Flow chamber 397 may include fluid channels such as inlet 398A and outlet 398B and the sample that would be in contact with the floating gate electrode 396. System 390 also includes primary gate electrode 400 coupled to aqueous buffer 402, such that aqueous buffer 402 capacitively couples floating gate electrode 396 to primary gate electrode 400.

FIGS. 25A-25F are conceptual illustrations of an example device 430 that uses capillary-driven flow to react a sample with the surface of a floating gate electrode 414. Device 430 may be similar to system 390 of FIG. 24. As shown in FIG. 24A, fluid channel 410 is defined by housing 412 and floating gate electrode 414. When the sample 420 is added to inlet 416, capillary action drives the flow of fluid in the direction of arrows 422 from inlet 416 to outlet 418. In other examples, a fluid pump may be used to drive the flow of fluid. FIG. 25B shows a top view of device 430 and fluid channel 410 of FIG. 25A. When sample 420 is added to reservoir 424, the sample is drawn into passage 426 and into fluid channel 410 where floating gate electrode 414 is located. Device 430 also includes discharge chamber 428.

As shown in FIG. 25C, sample 420 has flowed through to the outlet 418 such that the entire floating gate electrode 414 is covered by sample 420. FIG. 25D shows that at the same time as FIG. 25C, sample 420 has started to fill discharge chamber 428. FIG. 25E shows that the sample 420 is rinsed from the fluid channel 410 with an aqueous electrolyte 432. As shown in FIG. 25F, aqueous electrolyte 432 has started to enter discharge chamber 428 and forced all of sample 420 into the discharge chamber 428.

Figure 26:
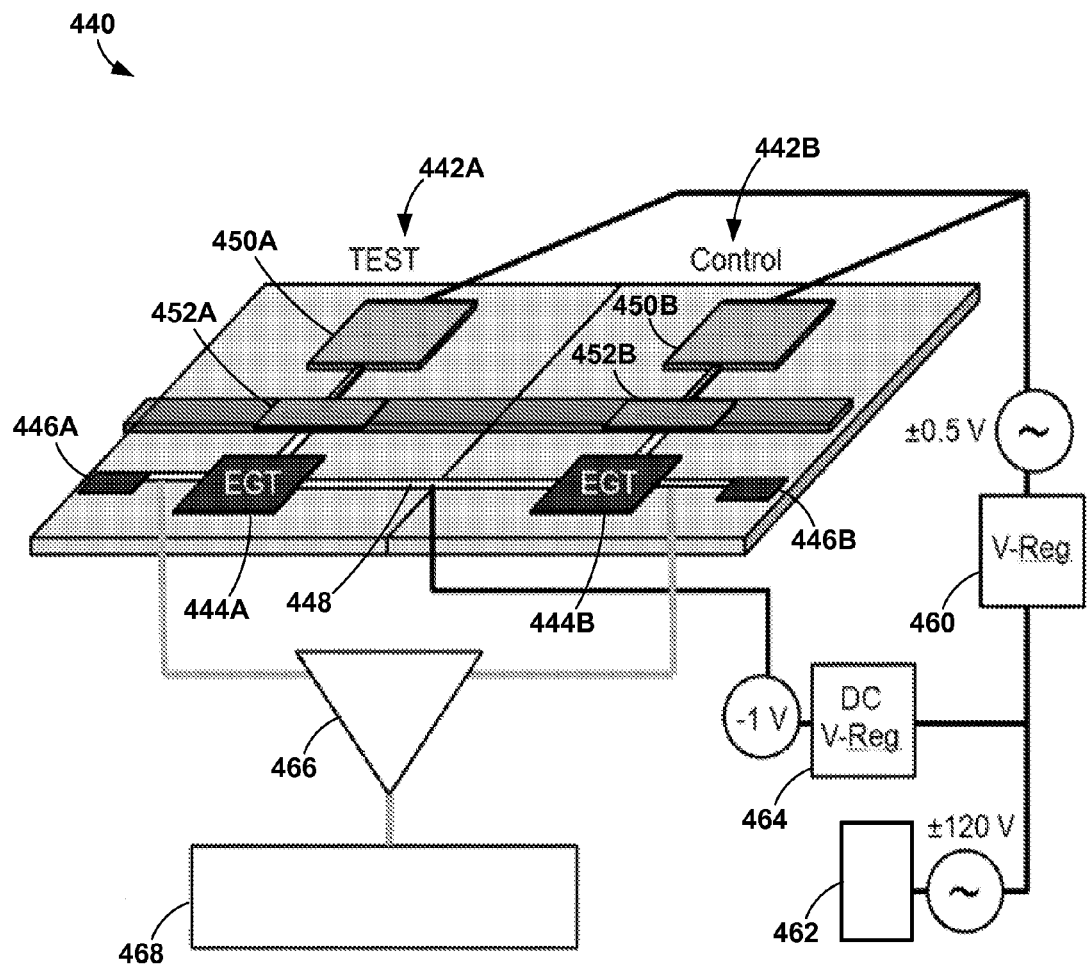
FIG. 26 is an example system for comparing a test sample to a control sample for determining whether the test sample includes a target molecule.

FIG. 26 is an example system 440 for comparing a test sample to a control sample for determining whether the test sample includes a target molecule. As shown in FIG. 26, system 440 includes test device 442A and control 442B, both separate transistors. Test device 442A includes drain electrode 446A, EGT 444A, floating gate electrode 452A, and primary gate electrode 450A. Similarly, control device 442B includes drain electrode 446B, EGT 444B, floating gate electrode 452B, and primary gate electrode 450B. Test device 442A and control device 442B may share a common source electrode 448.

Power source 462 (e.g., an electrical outlet or batter source) may drive voltage regulator 460 and voltage regulator 464. Voltage regulator 460 may apply an AC current to primary gate electrodes 442A and 442B, and voltage regulator 464 may apply a direct current to source electrode 448. After the control sample is applied to floating gate electrode 452B and the test sample (e.g., the sample that is being tested to determine if the target molecule is present), an amplifier (e.g., an op-amplifier 466) may compare the currents (e.g, an electrical property) from the drain electrodes 446A and 446B. A processor or comparator may be used to determine if the difference in current exceeds a threshold indicating that the target is present in the sample. Therefore, a processor or comparator, or op-amplifier 466, may output an indication of the measured electrical property (e.g., voltage or current) from drain electrodes 446A and 446B. In some examples, system 440 may be configured to determine, based on the measured electrical property, whether the target chemical composition of a molecule is present within the aqueous buffer by calculating a difference between the measured electrical property to a control electrical property of a second device similar to the first device, the first device comprising a sample of the target chemical composition of the molecule and the second device comprising a control solution void of the target chemical composition of the molecule, and determining that the target chemical composition of the molecule is present within the aqueous buffer when the difference exceeds a threshold. The threshold may be predetermined value based on expected changes to the electrical property when the target chemical composition is present and binds to the probe molecule.

User interface 468 may present an indication of the current difference and/or whether that current indicates that the target is present in the sample. User interface 468 may include a display device to provide a visual indication of the detection and/or a speaker to provide an audible indication of the detection. System 440 may be relatively inexpensive, simple to use, and implemented as a readily portable device.

Although system 440 is described as comparing the electrical property from the test sample to a control sample for determining whether or not the target molecule is present in the test sample, direct comparison to a control sample may not be required. In other examples, the measured electrical property from the test sample may be compared to a previously stored electrical property measured from an analyte known to have included the target molecule. In other examples, the measure electrical property from the test sample may be compared to the previous electrical property measured from the test device prior to the test sample being added to the reservoir or channel in contact with floating gate electrode 452A. The amount of change in the value of the electrical property may be indicative of whether or not the probe molecules associated with the floating gate electrode bound to target chemical compositions of a target molecule—binding indicating that the target molecule is present in the test sample.

Figure 27:
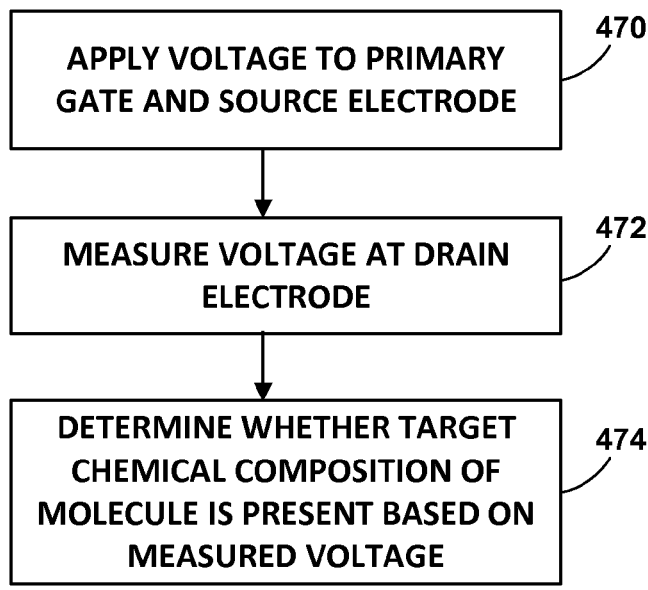
FIG. 27 is a flow diagram of an example method of determining whether a target chemical composition is present within a sample.

FIG. 27 is a flow diagram of an example method of determining whether a target chemical composition is present within a sample. As shown in FIG. 27, the device (e.g., device 20 or system 440) may apply a voltage to a source electrode and primary gate electrode (470). The device may measure the voltage (e.g., an electrical property) at drain electrode (472) and determine whether the target chemical composition of the target molecule is present in the sample based on measured voltage (474). For example, the measured voltage may be compared simultaneously to a control device output or a stored threshold representative of a sample testing positive for the target molecule. In some examples, the device may measure an electrical property different than voltage, such as electrical current.

Figure 28:
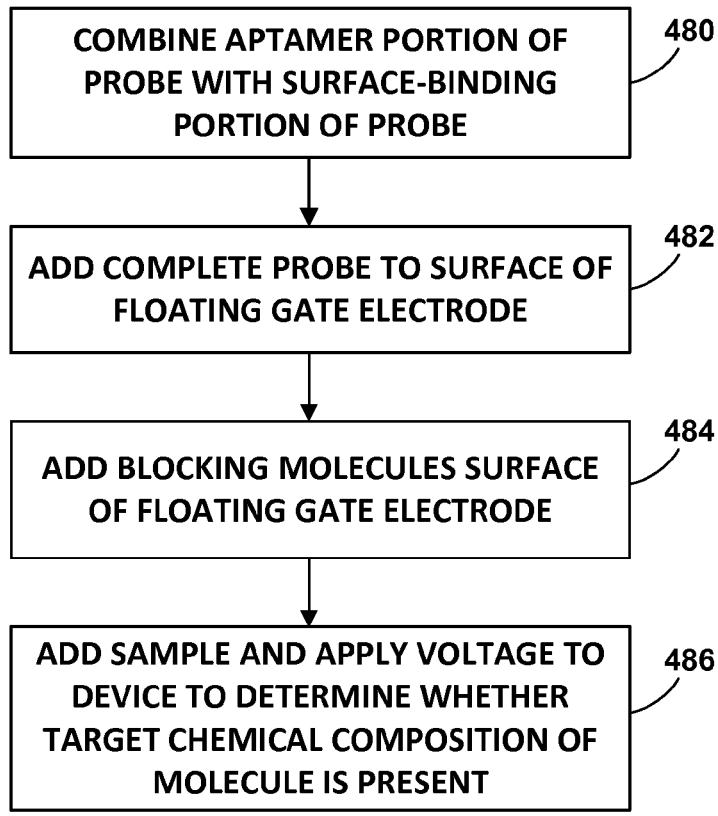
FIG. 28 is a flow diagram of an example method of using an example device that includes the EGT of FIGS. 1A-1D, as disclosed herein.

FIG. 28 is a flow diagram of an example method of using an example device (e.g., device 20 or system 440) that includes an EGT, as disclosed herein. As shown in FIG. 28, the user combines an aptamer portion of a probe molecule with the surface-binding portion of the probe molecule (480). The user may then add the complete probe molecule to the surface on the primary gate side of the floating gate electrode (482). Then, to minimize unbound molecules from affecting the voltage of the floating gate electrode, the user can add blocking molecules to the surface of the floating gate electrode (484). The user may then add the sample (i.e., the analyte) that may contain the target molecule and then apply voltage to the device to determine whether the target chemical composition of the molecule is present in the sample that is being tested (486). In some cases, the sample may be added to an aqueous buffer or already include an aqueous buffer.

As described above, some example devices can be adapted for the detection of target chemical compositions other than nucleic acids; for example, analytes that are not inherently charged, including polypeptides (e.g., a specific protein that may or may not be associated with a certain cell). During analysis of the molecular origin of the electronic signal (voltage offset), some example technologies respond to an induced charge in the floating gate electrode from the negatively charged phosphate backbone of DNA. In contrast, examples described herein that are configured to detect nucleic acids respond to an altered work function (alternatively, surface potential) of an electrode; the altered work function in turn originating from an altered charge, conductivity, polarizability, or electric dipole of molecules immobilized at the electrode surface. More importantly, the device responds to an altered interfacial capacitance of the floating gate interface brought about by analyte binding.

Transistors and sensors as described herein with respect to various examples are relatively simple, compact, and less sensitive to noise at the floating-gate electrode than some available floating-gate transistors. The active sensing surface can drive the device. In contrast, in available systems, these two interfaces are decoupled, and this can be disadvantageous because it increases the parasitic capacitance of the device and makes the device more susceptible to extraneous noise. Available devices often use extra encapsulation and/or a reference device to minimize error, which is not needed in devices according to some examples of the disclosure.

Some examples use an electrolyte such as an ion-gel in a potentiometric biosensor (rather than just a transistor). Available systems use conventional, solid-state dielectrics or water as the dielectric layer in potentiometric biosensors. In some examples, typical operating voltages may be ~10 V, with some possible operating voltages as low as 2 V due to a thin dielectric layer which is difficult to fabricate reliably. However, devices according to other examples may have an operating voltage of <1 V and can be simply printed.

Some examples of the devices described herein provide relatively high electronic sensitivity or change in semiconductor conductance per signal change from a binding event. Ionic conducting electronic insulators (i.e., ion-gels), as used in devices according to some examples, operate with very high capacitance, thereby allowing for very low operating voltages (<1 V). This in turn amounts to an improved electronic sensitivity, so that a potentiometric signal from a target molecule (i.e. voltage shift from DNA) causes significant changes in semiconductor conductance (as indicated by a changing drain current through a transistor).

Some examples are amenable to flexible, low-cost, and/or printable batteries and power sources due to the low operating voltage. This feature enhances the portability of the device of some examples, thereby enabling applications for field-ready devices used by untrained personnel.

Some examples can use simple photolithographic fabrication of one gold layer. The mobile ions in the ion-gel allow the gold electrodes to be constructed in a planar, side-gate architecture. This simplifies the photolithographic fabrication of electrodes to a one-layer deposition of patterned gold. In contrast, available CMOS or other multi-layer designs have multiple evaporation, etching, and deposition steps.

Some examples use solution-processable (i.e. printable), organic electronic materials. In contrast, some available devices may use inorganic (e.g. silicon) materials as either the semiconductor or dielectric layer or both. By using organic electronic materials, some devices can be fabricated at low temperatures (~60° C.), which may render such devices compatible with flexible, low-cost, plastic substrates. This can be important for portable devices, which need to be mechanically robust for use outside of a controlled, laboratory environment. Further, some examples can be multiplexed into an array which may require a relatively large-area footprint (e.g., an area larger than a silicon wafer). Such printed transistors are readily multiplexed into an array of biosensors used to analyze a complex mixture of biomolecules. While it is true that CMOS technology is multiplexable (as evident by integrated circuit technology), examples of the present disclosure are more easily adapted (at a lower cost) into a roll-to-roll fabrication process where the sensors are patterned over a wide range of spatial areas. This is, in principle, advantageous to the use of an array of sensors integrated with upstream microfluidic processes for sample preparation, as such an application may demand a large areal footprint.

EXAMPLES

The present disclosure can be further understood by reference to the following example which is offered by way of illustration. The present disclosure is not limited to the example given herein.

YOYO-1 dye can be purchased from Invitrogen. TE buffer can be used to store and transport DNA (10 mM Tris, 1 mM EDTA, pH=8.0) and phosphate buffered saline (PBS 1×) can be used as an aqueous electrolyte during device testing.

TABLE 1

DNA Sequences

| Name | Sequence |
| --- | --- |
| Probes | HS-$C_6H_{12}$-5'-GAG-AGA-CCG-GCG-CAC-AGA-GG-3' |
| COMP | 3'-CTC-TCT-GGC-CGC-GTG-TCT-CC-5' |
| MM1 | 3'-CTC-TCT-GGC-AGC-GTG-TCT-CC-5' |
| MM2 | 3'-CTC-TCG-GGC-CGC-GTT-TCT-CC-5' |
| MM3 | 3'-CTC-TCG-GGC-AGC-GTT-TCT-CC-5' |
| RAND | 3'-CGT-AAA-TGA-TCC-TTC-AAC-TA-5' |

In one example of device fabrication, the P3HT and ion-gel can be deposited with an aerosol jet printer available from Optomec Inc. P3HT can be dissolved in chloroform (1 mg/mL) then terpineol can be added (1:10 by volume) as a co-solvent. The ionic liquid can be mixed with SMS and ethyl acetate at a ratio of 1:9:90 by weight (EMIM/TFSI: SMS:Ethyl Acetate). The printing parameters for P3HT can include carrier gas of 10 cc/min, sheath gas of 20 cc/min. The printing parameters for the Ion-gel can include carrier gas of 15 cc/min, sheath gas of 25 cc/min. For both materials the stage velocity can be 1 mm/s, stage temperature of 60° C., nozzle diameter of 150 µm. The as fabricated device can be annealed at 120° C. for 30 minutes. A PDMS well can be then reversibly bonded (i.e. without plasma treatment) to device.

DNA can be stored in TE buffer at 100 µM. To immobilize the thiol-modified probes can be first reduced with dithiothreitol (DTT) (Sigma-Aldrich), purified via chromatography and diluted to 1 µM with TE buffer containing NaCl. To immobilize probes at a low density (2 pmol/cm$^2$) the probes can be spotted onto the floating gate electrode in TE buffer at 0.1 M NaCl for 2 hours. For medium density (7 pmol/cm$^2$) the probes can be spotted in TE buffer at 1.0 M NaCl for 2 hours. For high density (12 pmol/cm$^2$) the probes can be spotted in TE buffer at 1.0 M NaCl for 24 hours. The samples can be rinsed with TE buffer (no NaCl) then spotted with 1 mM Beta Mercapto Hexanol in DI water for 1 hour and rinsed with TE buffer. Complementary, mismatched or random DNA can be added at 1 µM (or as specified for complementary DNA) in TE buffer at 1.0 M NaCl for 1 hour and rinsed with TE buffer. Electrical measurements can be carried out with PBS 1× connecting the floating gate and gate electrodes. For fluorescent measurements, the samples can be immersed in a YOYO-1 solution diluted to 100 nM with TE buffer overnight (≥12 hours).

What is claimed is:

1. A device comprising:
   a semiconductor;
   an ionic conducting electronic insulator coupled to the semiconductor;
   a floating gate electrode comprising a first portion and a second portion, the first portion being coupled to the semiconductor via the ionic conducting electronic insulator;
   an aqueous buffer; and
   a primary gate electrode coupled to the second portion of the floating gate electrode via the aqueous buffer.

2. The device of claim 1, wherein the semiconductor comprises an organic semiconductor.

3. The device of claim 1, wherein the ionic conducting electronic insulator comprises a plurality of electrolyte dielectrics.

4. The device of claim 3, wherein the plurality of electrolyte dielectrics insulates one or more surfaces of the floating gate electrode.

5. The device of claim 1, wherein the second portion of the floating gate electrode comprises a surface chemically bound to a plurality of probe molecules.

6. The device of claim 5, wherein each probe molecule of the plurality of probe molecules comprises a first portion and a second portion, the first portion of each probe molecule being chemically bound to the surface of the floating gate electrode, and the second portion of each probe molecule comprising an affinity reagent configured to bind to a target chemical composition.

7. The device of claim 6, wherein the affinity reagent comprises at least one of a nucleic acid, a nucleic acid analog, a polypeptide, a protein, and an antibody.

8. The device of claim 5, wherein the surface of the second portion of the floating gate electrode comprises the plurality of probe molecules and a plurality of blocking molecules, the blocking molecules configured to prevent non-specific adsorption.

9. The device of claim 8, wherein the surface is chemically bound to the plurality of blocking molecules, the plurality of blocking molecules having a greater chemical affinity for the surface of the second portion of the floating gate electrode than unreacted probe molecules and displacing the unreacted probe molecules from the surface of the second portion of the floating gate.

10. The device of claim 8, wherein the blocking molecules comprise a chemical formula of $HS(CH_2)_6OH$.

11. The device of claim 1, wherein the second portion of the floating gate electrode comprises a surface functionalized with a self-assembled monolayer of molecules.

12. The device of claim 11, wherein the self-assembled monolayer of molecules comprises molecules selected from the group of molecules comprising 6-mercapto-1-hexanol and 3,3,4,4,5,5,6,6-nonaflouro-1-hexanol.

13. The device of claim 1, wherein the primary gate electrode is in direct contact with the aqueous buffer to capacitively couple the primary gate electrode to the second portion of the floating gate electrode via the aqueous buffer.

14. The device of claim 1, wherein the device comprises a transistor, the transistor comprising the semiconductor, the ionic conducting electronic insulator, the floating gate electrode, the aqueous buffer; and the primary gate electrode.

15. A system for detecting a molecule having a target chemical composition, the system comprising:
    a semiconductor;
    an ionic conducting electronic insulator coupled to the semiconductor;
    a floating gate electrode comprising a first portion and a second portion, the first portion being coupled to the semiconductor via the ionic conducting electronic insulator;
    an aqueous buffer;
    a primary gate electrode coupled to the second portion of the floating gate electrode via the aqueous buffer; and
    one or more circuits configured to measure an electrical property based on a voltage change over the ionic conducting electronic insulator, and output an indication of the electrical property.

16. The system of claim 15, wherein the semiconductor comprises an organic semiconductor.

17. The system of claim 15, wherein the ionic conducting electronic insulator comprises a plurality of electrolyte dielectrics.

18. The system of claim 17, wherein the plurality of electrolyte dielectrics insulates one or more surfaces of the floating gate electrode.

19. The system of claim 15, wherein the second portion of the floating gate electrode comprises a surface chemically bound to a plurality of probe molecules.

20. The system of claim 19, wherein each probe molecule of the plurality of probe molecules comprises a first portion and a second portion, the first portion of each probe molecule being chemically bound to the surface of the second portion of the floating gate electrode, and the second portion of each probe molecule comprising an affinity reagent configured to bind to the target chemical composition.

21. The system of claim 20, wherein the affinity reagent comprises at least one of a nucleic acid, a nucleic acid analog, a polypeptide, a protein, and an antibody.

22. The system of claim 19, wherein the surface of the second portion of the floating gate electrode comprises the plurality of probe molecules and a plurality of blocking molecules, the blocking molecules configured to prevent non-specific adsorption.

23. The system of claim 15, wherein the primary gate electrode is in direct contact with the aqueous buffer to capacitively couple the primary gate electrode to the second portion of the floating gate electrode via the aqueous buffer.

24. A method for detecting a molecule comprising a target chemical composition, the method comprising:
applying a voltage to a primary gate electrode of a device, the device comprising:
a source electrode and a drain electrode, the source electrode and the drain electrode being coupled to a semiconductor;
an ionic conducting electronic insulator coupled to the semiconductor;
a floating gate electrode comprising a first portion and a second portion, the first portion being coupled to the semiconductor via the ionic conducting electronic insulator; and
an aqueous buffer, wherein the primary gate electrode is coupled to the second portion of the floating gate electrode via the aqueous buffer;
measuring an electrical property at the drain electrode;
determining, based on the measured electrical property, whether the target chemical composition of the molecule is present within the aqueous buffer; and
outputting an indication of the determination.

25. The method of claim 24, wherein the ionic conducting electronic insulator comprises a plurality of electrolyte dielectrics.

26. The method of claim 25, wherein the plurality of electrolyte dielectrics insulates one or more surfaces of the floating gate electrode.

27. The method of claim 24, wherein the second portion of the floating gate electrode comprises a surface chemically bound to a plurality of probe molecules.

28. The method of claim 27, wherein each probe molecule of the plurality of probe molecules comprises a first portion and a second portion, the first portion of each probe molecule being chemically bound to the surface of the second portion of the floating gate electrode, and the second portion of each probe molecule comprising an affinity reagent configured to bind to the target chemical composition.

29. The method of claim 28, wherein the affinity reagent comprises at least one of a nucleic acid, a nucleic acid analog, a polypeptide, a protein, and an antibody.

30. The method of claim 27, wherein the surface of the second portion of the floating gate electrode comprises the plurality of probe molecules and a plurality of blocking molecules, the blocking molecules configured to prevent non-specific adsorption.

31. The method of claim 24, wherein measuring the electrical property at the drain electrode comprises measuring an electrical current.

32. The method of claim 24, wherein outputting the indication of the determination comprises displaying at least one of a visible or audible signal via a user interface.

33. The method of claim 24, wherein the device is a first device, and wherein determining, based on the measured electrical property, whether the target chemical composition of the molecule is present within the aqueous buffer comprises:
calculating a difference between the measured electrical property to a control electrical property of a second device similar to the first device, the first device comprising a sample of the target chemical composition of the molecule and the second device comprising a control solution void of the target chemical composition of the molecule; and
determining that the target chemical composition of the molecule is present within the aqueous buffer when the difference exceeds a threshold.

* * * * *